(12) United States Patent
Martin

(10) Patent No.: US 8,431,414 B2
(45) Date of Patent: *Apr. 30, 2013

(54) METHODS AND COMPOSITIONS FOR DIRECTED MICROWAVE CHEMISTRY

(75) Inventor: Mark T. Martin, Rockville, MD (US)

(73) Assignee: Mirari Biosciences, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/341,109

(22) Filed: Dec. 30, 2011

(65) Prior Publication Data

US 2012/0165209 A1 Jun. 28, 2012

Related U.S. Application Data

(60) Division of application No. 10/842,512, filed on May 11, 2004, now abandoned, which is a continuation-in-part of application No. 10/234,092, filed on Sep. 5, 2002, now Pat. No. 7,348,182, which is a continuation-in-part of application No. 09/968,517, filed on Oct. 2, 2001, now Pat. No. 7,351, 590.

(60) Provisional application No. 60/237,192, filed on Oct. 3, 2000.

(51) Int. Cl.
*G01N 33/543* (2006.01)

(52) U.S. Cl.
USPC .......................................................... 436/518

(58) Field of Classification Search .................. 436/518
See application file for complete search history.

(56) References Cited

U.S. PATENT DOCUMENTS

| | | |
|---|---|---|
| 3,455,842 A | 7/1969 | Cornelius et al. |
| 3,839,175 A | 10/1974 | Keyes |
| 4,221,680 A | 9/1980 | Hardwick |
| 4,340,672 A | 7/1982 | Kondo et al. |
| 4,575,485 A | 3/1986 | Sizto et al. |
| 4,683,195 A | 7/1987 | Mullis et al. |
| 4,683,202 A | 7/1987 | Mullis et al. |
| 4,745,077 A | 5/1988 | Holian et al. |
| 4,822,492 A | 4/1989 | Chao et al. |
| 4,822,566 A | 4/1989 | Newman |

(Continued)

FOREIGN PATENT DOCUMENTS

| | | |
|---|---|---|
| EP | 0 487 091 | 5/1992 |
| EP | 1 330 532 | 12/2011 |

(Continued)

OTHER PUBLICATIONS

Abati et al., "Looking forward in diagnostic pathology," Cancer, vol. 78, pp. 1-3 (1996).

(Continued)

*Primary Examiner* — Mark Shibuya
*Assistant Examiner* — Pensee Do
(74) *Attorney, Agent, or Firm* — Jenkins, Wilson, Taylor & Hunt, P.A.

(57) ABSTRACT

The present invention concerns a novel means by which chemical preparations can be made. Reactions can be accelerated on special cartridges using microwave energy. The chips contain materials that efficiently absorb microwave energy causing chemical reaction rate increases. The invention is important in many chemical transformations including those used in protein chemistry, in nucleic acid chemistry, in analytical chemistry, and in the polymerase chain reaction.

20 Claims, 12 Drawing Sheets

1. Dielectric Surface
2. Surface-bound reactants 1. reagent capture membrane (upper layer)
2. underlying inert support (optional middle layer)
3. dielectric layer (lower layer)

U.S. PATENT DOCUMENTS

| | | | |
|---|---|---|---|
| 4,880,752 | A | 11/1989 | Keck et al. |
| 5,285,040 | A | 2/1994 | Brandberg et al. |
| 5,350,686 | A | 9/1994 | Jhingan |
| 5,403,747 | A | 4/1995 | Akins et al. |
| 5,427,779 | A | 6/1995 | Elsner et al. |
| 5,451,428 | A | 9/1995 | Rupp |
| 5,478,748 | A | 12/1995 | Akins et al. |
| 5,496,701 | A | 3/1996 | Pollard-Knight |
| 5,689,008 | A | 11/1997 | Satyapal et al. |
| 5,767,470 | A | 6/1998 | Cha |
| 5,780,578 | A | 7/1998 | Mashelkar et al. |
| 5,846,843 | A | 12/1998 | Simon |
| 5,869,349 | A | 2/1999 | Lin et al. |
| 5,911,941 | A | 6/1999 | Rokhvarger et al. |
| 5,922,537 | A | 7/1999 | Ewart et al. |
| 5,939,614 | A | 8/1999 | Walters et al. |
| 5,985,356 | A | 11/1999 | Schultz et al. |
| 6,004,534 | A | 12/1999 | Langer et al. |
| 6,011,247 | A | 1/2000 | Grillo et al. |
| 6,029,498 | A | 2/2000 | Walters et al. |
| 6,034,775 | A | 3/2000 | McFarland et al. |
| 6,093,302 | A | 7/2000 | Montgomery |
| 6,099,864 | A | 8/2000 | Morrison et al. |
| 6,140,045 | A | 10/2000 | Wohlstadter et al. |
| 6,159,681 | A | 12/2000 | Zebala |
| 6,180,415 | B1 | 1/2001 | Schultz et al. |
| 6,235,241 | B1 | 5/2001 | Catt et al. |
| 6,255,477 | B1 | 7/2001 | Kleiber et al. |
| 6,316,153 | B1 | 11/2001 | Goodman et al. |
| 6,355,491 | B1 | 3/2002 | Zhou et al. |
| 6,413,783 | B1 | 7/2002 | Wohlstadter et al. |
| 6,630,358 | B1 | 10/2003 | Wagner et al. |
| 7,348,182 | B2 * | 3/2008 | Martin et al. ............... 436/518 |
| 7,351,590 | B2 * | 4/2008 | Martin ............... 436/518 |
| 7,718,445 | B2 * | 5/2010 | Martin ............... 436/518 |
| 8,008,067 | B2 | 8/2011 | Geddes et al. |
| 8,034,633 | B2 | 10/2011 | Geddes |
| 2002/0197645 | A1 | 12/2002 | Martin |
| 2003/0082633 | A1 | 5/2003 | Martin |
| 2004/0209303 | A1 | 10/2004 | Martin |
| 2005/0191708 | A1 | 9/2005 | Saul |
| 2008/0248489 | A1 | 10/2008 | Martin |

FOREIGN PATENT DOCUMENTS

| | | |
|---|---|---|
| GB | 1 363 526 | 8/1974 |
| JP | S64-002608 | 1/1989 |
| JP | H03-238895 | 10/1991 |
| JP | H04-260472 | 9/1992 |
| JP | H06-043161 | 2/1994 |
| JP | H08-105892 | 4/1996 |
| JP | H09-255365 | 9/1997 |
| JP | H09-297138 | 11/1997 |
| JP | 11-171668 | 6/1999 |
| JP | 4833498 | 9/2011 |
| WO | WO02/29076 | 4/2002 |
| WO | WO2004/023144 | 3/2004 |

OTHER PUBLICATIONS

Adeyeye and Price, Pharm. Res., vol. 8, pp. 1377-1383 (1991).
Alexandratos and Natesan, "Coordination Chemistry of Phosphorylated Calixarenes and Their Application to Separations Science," Ind. Eng. Chem. Res., vol. 39, pp. 3998-4010 (Sep. 14, 2000).
Alves da Silva et al., "Photopolymerization of acrylamide onto magnetite particles: preparation of magnetic supports for enzyme immobilization," Materials Letters, vol. 11, pp. 96-100(1991).
Antia & Govind, "Applications of binderless zeolite-coated monolithic reactors," Applied Catalysis A: General, vol. 131, pp. 107-120 (1995).
Anzai et al., "Enzyme sensors prepared by layer-by-layer deposition of enzymes on a platinum electrode through avidin-biotin interaction," Sensors and Actuators, vol. 52, No. 1-2, pp. 3-9 (Sep. 15, 1998).
Aslan et al., "Microwave-accelerated metal-enhanced fluorescence: application to detection of genomic and exosporium anthrax DNA in 30 seconds," Analyst. vol. 132 pp. 1130-1138 (2007).
Aslan et al., "Fast and sensitive DNA hybridization assays using microwave-accelerated metal-enhanced fluorescence," Biochemical and Biophysical Research Communications. vol. 348 pp. 612-617 (2006).
Badzian et al., "Nucleation and growth phenomena in chemically vapor-deposited diamond coatings," Surface and Coatings Technology, vol. 36, No. 1-2, pp. 283-293 (Dec. 1, 1988).
Basu and Basu, Liposome Methods and Protocols, Humana Press, Totowa, NJ, pp. 3-16 (2002).
Baziard et al., "Cross-linking under microwaves (2.45 GHz) of aluminum powder-epoxy resin composites I. Electrical power dependence," European Polymer Journal, vol. 24, p. 873 (1988).
Becker and Gartner, Electrophoresis, vol. 21, pp. 12-26 (2000).
Beebe et al, Annu. Rev. Biomed., vol. 4, pp. 261-286 (2002).
van Bekkum et al., "Supported Zeolite Systems and Applications," Studies in Surface Science and Catalysis, Elsevier Science B.V., Amsterdam, NI, vol. 85, pp. 509-542 (1994).
Blackwell, H. E., Org. Biomol. Chem., vol. 1, pp. 1251-1255 (2003).
Boon et al., "Microwave Cookbook of Pathology," Columb Press, Leiden. vol. 17, pp. 1-219 (1989).
Borchart et al., "Synthetic receptor binding elucidated with an encoded combinatatorial library," Journal of American Chemical Society, vol. 116, p. 373 (1994).
Borman, "Combinatorial Chemistry," Chemical and Engineering News, pp. 49-58 (Aug. 21, 2001).
Bose et al., "More Chemistry in Microwave," Chemtech, vol. 27, No. 9, pp. 18-25 (1997).
Bowie et al., "Analytical applications of liquid phase chemiluminescence reactions—a review," Journal of Bioluminescence and Chemiluminescence, vol. 11, pp. 61-90 (1996).
Bradley, D., "The Nuke's the Thing for Synthesis," Modern Drug Discovery, vol. 4, No. 8, pp. 32-36 (2001).
Bram et al., "Alkylation of Potassium Acetate in 'Dry Media' Thermal Activation in Commercial Microwave Ovens," Tetrahedron, vol. 46, p. 5167 (1990).
Bram et al., "Anthraquinone Microwave-Induced Synthesis in Dry Media in Domestic Ovens," Chem. Ind., p. 396 (1991).
Breslow et al., "Optimization of metallocene substrates for beta-cyclodextrin reactions," Journal of American Chemical Society, vol. 105, p. 2739 (1983).
Buffler et al., "Microwave processing of materials," Materials Research Society Symposium Proceedings, vol. 430, p. 85 (1996).
Burow et al., "Molecular imprinting: Synthesis of polymer particles with antibody-like binding characteristics for glucose oxidase," Biochemical and Biophysical Research Communications, vol. 227, p. 419 (1996).
Burtsoff, Modern Drug Discovery, vol. 7, pp. 55-56 (2004).
Bystrom et al., "Selective reduction of steroid 3- and 17-ketones using LiAlH4 activated template polymers," Journal of the American Chemical Society, vol. 115, p. 2081 (1993).
Cahnman, H., "Infrared: How Does it Work?" downloaded Jul. 25, 2006 from http://www.cassosolar.com/sales/how_it_works.htm.
Cantarella et al., "Cellulose Hydrolysis and Fermentation," Proceedings of a CEC Workshop, pp. 186-195 (1992).
Chen and Chen, Electrophoresis, vol. 21, pp. 165-170 (2000).
Cho and Bailey, "Immobilization of Enzymes on Activated Carbon: Properties of Immobilized Glucoamylase, Glucose Oxidase, and Gluconolactonase," Biotechnology and Bioenginerring, vol. 20, pp. 1651-1665 (1978).
Committee on Microwave Processing of Materials, National Materials-Advisory Board, Commission on Engineering and Technical Systems, and National Research Council (1994) Microwave Processing of Materials. Washington, DC, National Academy Press.
Communication Pursuant to Article 94(3) EPC corresponding to European Patent Application No. 01 979 344.7-2404 dated Jan. 29, 2010.
Communication Pursuant to Article 94(3) EPC corresponding to European Patent Application No. 01 979 344.7-2404 dated Feb. 17, 2009.
Constans, A., The Scientist, pp. 43-45 (Nov. 2003).
Cooper, "Applications of microarray technology in breast cancer research," Breast Cancer Research, vol. 3, pp. 158-175 (2001).

Cornelis et al., "Oxidation of Alcohols by Clay-Supported Iron (III) Nitrate; A New Efficient Oxidizing Agent," Synthesis, vol. 1980, pp. 849-850 (Oct. 1980).

Dai et al., "Imprint Coating: a novel synthesis of selective functionalized ordered mesoporous sorbents," Angewandte Chemie International Edition, vol. 38, p. 1235 (1999).

Decision to grant a European patent pursuant to Article 97(1) EPC corresponding to European Patent Application No. 01979344.7-2404/1330532, dated Nov. 17, 2011.

Dickert et al., "Molecularly imprinted polymers for optichemical sensors," Advanced Materials, vol. 8, p. 987 (1996).

Dolle et al., "Comprehensive survey of combinatorial library synthesis: 1999," Journal of Combinatorial Chemistry, vol. 2, pp. 383-433 (2000).

Donbrow, "Microcapsules and Nanoparticles in Medicine and Pharmacy," CRC Press, Boca Raton, FL, pp. 1-14 (1991).

Draghici et al., "Experimental design, analysis of variance and slide quality assessment in gene expression arrays," Current Opinion in Drug Discovery and Development, vol. 4, pp. 332-337.

Drummond et al., Pharm. Rev., vol. 51, pp. 691-743 (1999).

Durm et al., "Optimized Fast-FISH with α—satellite probes: acceleration by microwave activation," Brazilian Journal of Medical and Biological Research. vol. 30 pp. 15-23 (1997).

Duzgunes, N., Methods Enzymol., vol. 367, pp. 99-110 (2003).

Duzgunes, N., Methods Enzymol., vol. 373, pp. 260-277 (2004).

Fermer et al., Eur. J. Pharm. Sci., vol. 18, pp. 129-132 (2003).

Fitzgerald, D. A., The Scientist, vol. 16, pp. 40-42 (2002).

Fleischer, C.T. & Boos, K.-S. (2001) American Laboratory, May 30, 20-25.

Fodor et al., "Multiplexed Biochemical Assays with Biological Chips," Nature, vol. 3, pp. 555-556 (1993).

Folkman, "Angiogenesis and an inhibition: an overview," EXS, vol. 79, pp. 1-8 (1997).

Fong et al., 79, pp. 271-276 (2002).

Freeman et al., "Quantitative RT-PCR: Pitfalls and potential," BioTechniques, vol. 26, pp. 112-125 (1985).

Futaki, S., "Peptide Ion Channels: Design and Creation of Function," Biopolymers (Peptide Science), vol. 47, pp. 75-81 (1998).

Gabriel et al., "Dielectric Parameters Relevant to Microwave Dielectric Heating," Chemical Society Reviews, vol. 27, pp. 213-224 (1998).

Gallop et al., "Applications of Combinatorial Technologies to Drug Discovery. 1. Background and Peptide Combinatorial Libraries," Journal of Medicinal Chemistry, vol. 37, No. 9, pp. 1233-1251 (1994).

Giordano et al., Anal. Biochem., vol. 291, pp. 124-132 (2001).

Glad et al., "Use of Silane monomers for molecular imprinting and enzyme entrapment in polysiloxane-coated porous silica," Journal of Chromatography, vol. 347, p. 11 (1985).

Gloffke, The Scientist, vol. 17, No. 8, pp. 41-43 (2003).

Gordon et al., "Applications of Combinatorial Technologies to Drug Discovery. 2. Combinatorial Organic Synthesis, Library Screening Strategies and Future Directions," Journal of Medicinal Chemistry, vol. 37, No. 10, pp. 385-401 (1994).

Gregoriadis, G., "Liposome Technology, vol. III, Targeted Drug Delivery and Biological Interaction," CRC Press, Boca Raton, FL, pp. 137-155 (1983).

Gregoriadis, G., Liposome Technology, vol. I, Preparation of Liposomes, CRC Press, Boca Raton, FL, pp. 1-18 (1983).

Gu et al., "Photo-fries reactions of 1-Naphthyl esters in cation-exchanged zeolite Y and Polyethylene media," Journal of American Chemical Society, vol. 121, p. 9467 (1999).

Hailing et al., "Hydrolysis of Lactose in Milk by Lactase Immobilized to a Non-Porous Magnet Support," European Journal of Applied Microbiology and Biotechnology, vol. 8, No. 1-2, pp. 27-36 (1979).

Hansen and Quake, Curr. Opin. Struct. Biol., vol. 13, pp. 538-544 (2003).

Harada, A., "Construction of Supramolecular Stuctures from Cyclodextrins and Polymers," Carbohydrate Polymers, vol. 34, No. 3, pp. 183-188 (Dec. 20, 1997).

Harkin, "Uncovering functionally relevant signaling pathways using microarray-based expression profiling," Oncologist, vol. 5, pp. 501-507 (2000).

Hasted, "Aqueous dielectrics," Chapman & Hall, London, pp. 1-255 (1973).

Hergenrother et al., "Small-Molecule Microarrays: Covalent Attachment and Screening of Alcohol-Containing Small Molecules on Glass Slides," Journal of American Chemical Society, vol. 122, pp. 7849-7850 (2000).

Hilpert et al., "Anti-c-myc Antibody 9E10: Epitope Key Positions and Variability Characterized Using Peptide Spot Synthesis on Cellulose," Protein Engineering, vol. 14, pp. 803-806 (2001).

Hjerpe et al., 20, 388-396.(1988).

Hoffman, A. S., Clin. Chem., vol. 46, pp. 1478-1486 (2000).

Holzworth et al., "Enhanced microwave heating of nonpolar solvents by dispersed magnetic nanoparticles," Industrial and Engineering Chemistry Research, vol. 37, p. 2701 (1998).

Huhmer et al., "Noncontact infrared-mediated thermocycling for effective polymerase chain reaction amplification of DNA in Nanoliter volumes," Analytical Chemistry, vol. 72, pp. 5507-5512 (2000).

Issued Patent corresponding to Australian Patent Application No. 2003254187 dated Oct. 29, 2009.

Jacobs et al., "Combinatorial Chemistry—Applications of Light-Directed Chemical Synthesis," Trends in Biotechnology, vol. 12, pp. 19-26 (1994).

Jain et al., Anal. Biochem., vol. 311, pp. 84-86 (2002).

Jansen et al., "Preparation of Coatings of Molecular Sieve Crystals for Catalysis and Separation," Studies in Surface Science and Catalysis, Elsevier Science B.V., Amsterdam, NI, vol. 85, pp. 215-250 (1994).

Jansen et al., "Advanced zeolite science and applications," Jansen et al. eds., Elsevier, New York, pp. 215-250 (1994).

Jeong and Gutowska, Trends Biotechnol., vol. 20, pp. 305-311 (2002).

Jiang et al., "Template-directed preparation of macroporous polymers with oriented and crystalline arrays of voids," Journal of American Chemical Society, vol. 121, p. 11630 (1999).

Jin et al., "Application of microwave techniques in analytical chemistry," Trends in Analytical chemistry, vol. 18, pp. 479-484 (1999).

Johnson, "All's Well that Ends Well: a Profile of Specialty Microwell Plates," The Scientist, vol. 13, p. 16 (1999).

Jones, "Membrane immobilization of nucleic acids: Part 1: Substrates," IVD Technology, vol. 7, No. 6, pp. 50-54 (2001).

Kappe, "High-Speed Combinatorial Synthesis Utilizing Microwave Irradiation," Current Opinion in Chemical Biology, vol 6, pp. 314-320 (2002).

Kappe, "Speeding up Solid-Phase Chemistry by Microwave Irradiation: a Tool for High-Throughput Synthesis," American Laboratory, vol. 23, pp. 13-19 (2001).

Kawakami et al., "Immobilization of Glucose Oxidase of Polymer Membranes Treated by Low-Temperature Plasma," Biotechnology and Bioengineering, vol. 32, No. 3, pp. 369-373 (1988).

Kempe et al, "An approach towards surface imprinting using the enzyme ribonuclease A," Journal of Molecular Recognition, vol. 8, p. 35 (1995).

Kidwai et al., "A novel enzymatic synthesis of 2-substituted Naphtho[2,1-b]-pyran-3-ones using microwaves," Indian Journal of Chemistry Section B: Organic Chemistry including Medicinal Chemistry, vol. 37B, p. 963 (1998).

Kitayama et al., "Initial Intermittent Microwave Irradiation for Fluorescence In Situ Hybridization Analysis in Paraffin-Embedded Tissue Sections of Gatronintestinal Neoplasia," Laboratory Investigation. vol. 80, No. 5 pp. 779-781 (2000).

Kok and Boon, Histochem. J., vol. 22, pp. 381-388 (1990).

Kono, K., Adv. Drug Deliv. Rev., vol. 53, pp. 307-319 (2001).

Korbel et al., "Reaction Microarrays: a Method for Rapidly Determining the Enantiomeric Excess of Thousands of Samples," Journal of American Chemical Society, vol. 123, pp. 361-362 (2001).

Kramer et al., "Synthesis and Screening of Peptide Libraries on Continuous Cellulose Membrane Supports," Methods in Molecular Biology, vol. 87, pp. 25-39 (1998).

Kreider, K.G., "Thin Film Thermocouples for High Temperature Measurement," NIST, Springfield, VA (1989).

Kricka, et al., "Nucleic acid detection technologies—labels strategies, and formats," Clinical Chemistry, vol. 45, pp. 453-458 (1999).

Krishnan et al., "Solid-phase extraction techniques for the analysis of biological samples," Journal of Pharmaceutical and Biomedical Analysis, vol. 12, pp. 287-294 (1994).

Kubrakova, I.V., "Effect of microwave radiation on physiochemical process in solutions and heterogeneous systems: applications in analytical chemistry," Journal of Analytical Chemistry, vol. 55, pp. 1113-1122 (2000).

Laszlo, T.S., "Industrial applications of microwaves," The Physics Teacher, pp. 570-579 (Nov. 1980).

Latchman, D.S. (1995) PCR Applications in Pathology. Principles and Practice. NY, Oxford Univ. Press.

Laurell et al., "Enhanced Enzyme Activity in Silicon Integrated Enzyme Reactors Utilizing Porous Silicon as the Coupling Matrix," Sensors and Actuators B, vol. 31, No. 3, pp. 161-165 (Mar. 1, 1996).

Leitzel et al., "Detection of cancer cells in peripheral blood of breast cancer patients using reverse transcription-polymerase chain reaction for epidermal growth factor receptor," Clinical Cancer Research, vol. 4, pp. 3037-3043 (1998).

Lennon, G.G., "High-throughput gene expression analysis for drug discovery," Drug Discovery Today, vol. 5, pp. 59-66 (2000).

Leonhardt et al., "Enzyme-mimicking polymers exhibiting specific substrate binding and catalytic functions," Reactive Polymers, vol. 6, p. 285 (1987).

Leong and Milios, J. Pathol. vol. 148, pp. 183-187 (1986).

Lesney, M. S., Modern Drug Discovery, vol. 5, pp. 37-41 (2002).

Lew et al., "Increasing rates of reaction: microwave-assisted organic synthesis for combinatorial chemistry," Journal of Combinatorial Chemistry, vol. 4, pp. 95-105 (2002).

Lidstrom et al., "Enhancement of combinatorial chemistry by microwave-assisted organic synthesis," Combinatorial Chemistry and High Throughput Screening, vol. 5, pp. 441-458 (2002).

Lidstrom et al., "Microwave-assisted organic synthesis—a review," Tetrahedron, vol. 57, pp. 9225-9283 (2001).

MacBeath et al., "Printing small molecules as microarrays and detecting protein—ligand interactions en Masse," Journal of American Chemical Society, vol. 121, pp. 7967-7968 (1999).

Makote et al., "Dopamine recognition in templated silicate films," Chemical Communications, vol. 3, p. 425 (1998).

Marx, J., "DNA arrays reveal cancer in its many forms," Science, vol. 289, pp. 1670-1672 (2000).

Mathew-Krotz et al., "Imprinted polymer membranes for the selective transport of targeted neutral molecules," Journal of American Chemical Society, vol. 118, p. 8134 (1995).

Maugard et al., Biotechnol. Lett., vol. 25, 623-629 (2003).

Maugh, T. H., "Semisynthetic enzymes are new catalysts," Science, vol. 222, pp. 151-153 (1984).

Maugh, T.H., "Catalysts that break nature's monopoly," Science, vol. 221, pp. 351-354 (1983).

Maugh, T.H., "Need a catalyst? Design an enzyme," Science, vol. 223, pp. 269-271 (1983).

McDonald et al., Electrophoresis, vol. 21, pp. 27-40 (2000).

McPherson and Moller, "PCR," Bios Scientific Publishers, Oxford, UK (2000).

Mehvar, R., "Modulations of the Pharmacokinetics and Pharmacodynamics of Proteins by Polyethylene Glycol Conjunctions," Journal of Pharmacy and Pharmaceutical Sciences, vol. 3, No. 1, pp. 125-136 (Jan. 1, 2000).

Microwave Processing of Materials V. In Mat. Res. Soc. Symp. Proc. 430, Iskander, MF et al., eds. (1996).

Mingos et al., "Applications of microwave dielectric heating effects to synthetic problems in chemistry," Chemical Society Reviews, vol. 20, pp. 1-47 (1991).

Mokaya, R., "Ultrastable mesoporous aluminosilicates by grafting routes," Angewandte Chemie International Edition, vol. 38, p. 2930 (1999).

Narrlow et al., "Acrylic polymer preparations containing recognitions sites obtained by imprinting with substrates," Journal of Chromatography, vol. 229, p. 29 (1984).

Nataranjan et al., Bioelectromagnetics, vol. 23, pp. 271-277 (2002).

Nesatyy et al., "Microwave-assisted protein staining: mass spectrometry compatible methods for rapid protein visualization," Rapid Communications in Mass Spectrometry, vol. 16, pp. 272-280 (2002).

Newton and Graham, "PCR," Springer-Verlag, New York (1997).

Noguchi et al., "Comparison of Enzyme Immunoassay with Dextran-coated Charcoal Method in the Determination of Progesterone Receptor in Breast Cancer Cytosols," Eur. J. Cancer Clin. Oncol., vol. 24, pp. 1715-1719 (1988).

Notice of Allowance corresponding to U.S. Appl. No. 09/968,517 (U.S. Patent No. 7,351,590) dated Jan. 16, 2008.

Notice of Allowance corresponding to U.S. Appl. No. 09/968,517 (U.S. Patent No. 7,351,590) dated Oct. 5 2007.

Notice of Allowance corresponding to U.S. Appl. No. 10/234,092 (U.S. Patent No. 7,348,182) dated Oct. 2, 2007.

Notice of Allowance corresponding to U.S. Appl. No. 10/234,092 (U.S. Patent No. 7,348,182) dated Jan. 16, 2008.

Notice of Allowance corresponding to U.S. Appl. No. 11/105,460 dated Jul. 5, 2012.

Notice of Allowance corresponding to U.S. Appl. No. 12/059,427 (U.S. Patent No. 7,718,445) dated Dec. 29, 2009.

Notice of Intent to Grant corresponding to European Patent Application No. 01979344.7-2404 dated Jun. 22, 2011.

Notice of Intent to Grant/Decision of Appeal corresponding to Japanese Patent Application No. 2004-534253 dated Mar. 26, 2012.

O'Shannessy et al., "Molecular imprinting of amino acid derivatives at low temperature (0°C) using photolytic homolysis of azobisnitriles," Analytical Biochemistry, vol. 177, p: 144 (1989).

O'Shannessy et al., "Recent advances in the preparation and use of molecularly imprinted polymers for enantiomeric resolution of amino acid derivatives," Journal of Chromatography, vol. 470, p. 391.

Office Communication corresponding to U.S. Appl. No. 09/968,517 (U.S. Patent No. 7,351,590) dated Apr. 5, 2005.

Office Communication corresponding to U.S. Appl. No. 09/968,517 (U.S. Patent No. 7,351,590) dated Jan. 9, 2006.

Office Communication corresponding to U.S. Appl. No. 09/968,517 (U.S. Patent No. 7,351,590) dated Nov. 3, 2006.

Office Communication corresponding to U.S. Appl. No. 09/968,517 (U.S. Patent No. 7,351,590) dated May 15, 2007.

Office Communication corresponding to U.S. Appl. No. 10/234,092 (U.S. Patent No. 7,348,182) dated Nov. 9, 2006.

Office Communication corresponding to U.S. Appl. No. 10/234,092 (U.S. Patent No. 7,348,182) dated May 15, 2007.

Office Communication corresponding to U.S. Appl. No. 10/842,512 dated Oct. 19, 2005.

Office Communication corresponding to U.S. Appl. No. 10/842,512 dated Jan. 8, 2007.

Office Communication corresponding to U.S. Appl. No. 10/842,512 dated Oct. 3, 2007.

Office Communication corresponding to U.S. Appl. No. 10/842,512 dated Jan. 24, 2008.

Office Communication corresponding to U.S. Appl. No. 10/842,512 dated Oct. 14, 2009.

Official Action corresponding to U.S. Appl. No. 10/842,512 dated Oct. 5, 2011.

Office Communication corresponding to U.S. Appl. No. 11/105,460 dated Oct. 6, 2009.

Office Communication corresponding to U.S. Appl. No. 11/105,460 dated Apr. 16, 2010.

Office Communication corresponding to U.S. Appl. No. 12/059,427 dated Dec. 12, 2008.

Office Communication corresponding to U.S. Appl. No. 12/059,427 dated Sep. 17, 2009.

Office Communication corresponding to Canadian Patent Application No. 2,498,005 dated Feb. 29, 2012.

Office Communication corresponding to the European Patent Application No. 03 794 447.7-2404 dated Dec. 17, 2010.

Office Communication corresponding to the European Patent Application No. 01979344.7-2404 dated Nov. 17, 2011 (decision to grant).

Office Communication corresponding to the European Patent Application No. 01979344.7-2404 dated Dec. 29, 2010.

Office Communication corresponding to the European Patent Application No. 01979344.7-2404 dated Feb. 15, 2007.

Official Communication corresponding to an Australian Patent Application No. 2003254187 dated Jun. 2, 2008.

Official Communication corresponding to Japanese Patent Application No. 2002-532645 dated Jun. 1, 2010.

Official Communication corresponding to Japanese Patent Application No. 2004-534253 dated Jun. 1, 2010.
Official Communication corresponding to Japanese Patent Application No. 2004-534253 dated Oct. 7, 2008.
Official Communication corresponding to Japanese Patent Application No. 2002-532645 dated Mar. 25, 2008.
Official Communication corresponding to Canadian Patent Application No. 2,498,005 dated Feb. 24, 2011.
Official Communication corresponding to Canadian Patent Application No. 2,498,005 dated May 13, 2010.
Olmedo et al., "Microwave absorbing materials based on conducting polymers," Advanced Materials, vol. 5, p. 373 (1993).
Ostro, M. J., "Liposome. From Biophysics to Therapeutics," Marcel Dekker, New York, pp. 297-298 (1987).
Pasinetti, G.M., "Use of cDNA microarray in the search for molecular markers in the onset of Alzheimer's disease dementia," Journal of Neuroscience Research, vol. 65, pp. 471-476 (2001).
Robinson, J.K., "New Molecular Beacon Technology," American Laboratory, vol. 28, p. 34. (Dec. 2000).
Roda et al., "Bio- and Chemiluminescence in Bioanalysis," Fresenius Journal of Analytical Chemistry, vol. 3, pp. 752-759 (2000).
Roper et al., vol. 75, pp. 4711-4717 (2003).
Rouhi, A.M., "Boxed in: chemistry in confined spaces," Chemical and Engineering News, pp. 40-47 (Aug. 27, 2001).
Roussy et al. "Foundations and industrial applications of microwave and radio frequency fields," John Wiley & Sons, NY., pp. 445-466 (1995).
Roy and Gupta, Chemistry and Biology, vol. 10, pp. 1161-1171 (2003).
Saaristo et al., "Mechanisms of angiogenesis and their use in the inhibition of tumor growth and metastasis ," Oncogene, vol. 19, pp. 6122-6129 (2000).
Schena et al., "Quantitative monitoring of gene expression patterns with a complementary DNA microarray," Science, vol. 270, pp. 467-470 (1995).
Schmalzing et al., "Capillary electrophoresis-based immunoassays," Electrophoresis, vol. 21, pp. 3919-3930 (2000).
Seiden et al. "PCR- and RE-PCR-based methods of tumor detection: potential applications and clinical implications," Important advances Oncol. Lippincott-Raven, Philadelphia, PA. pp. 191-204 (1996).
Shi et al., "Template-imprinted nanostructured surfaces for protein recognition," Nature, vol. 398, pp. 593-597 (1999).
Sidransky, D., "Nucleid acid-based methods for the detection of cancer," Science, vol. 278, pp. 1054-1058 (1997).
Slap, S. E., Am. Biotechnol. Laboratory, November, 40 (2003).
Slyadnev et al., "Photothermal temperature control of a chemical reaction on a microchip using an infrared diode laser," Analytical Chemistry, vol. 73, pp. 4037-4044 (2001).
Stein et al. "Microwave processing of materials," Committee on microwave Processing of Materials; National Materials Advisory Board; Commission on Engineering and Technical Systems; and National Research Council; Microwave processing of Materials, Washington, DC, National Academy Press (1994).
Stillman and Tonkinson, BioTechniques, vol. 29, p. 630 (2000).
Supplementary European Search Report corresponding to the European Patent Application No. 01979344.7-2404 / 1535071 dated Aug. 3, 2010.
Surrmeijer et al., Histochem. J., vol. 22, pp. 341-346 (1990).
Suwa et al., "Magnetic Resonance Imaging of Esophageal Squamous Cell Carcinoma Using Magnetite Particles Coated with Anti-Epidermal Growth Factor Receptor Antibody," Int. J. Cancer, vol. 75, pp. 626-634 (1998).
Tarasevich, "293—Electrocatalysis of a Gathodie Oxygen Reduction by Laccase," Bioelectrochemistry and Bioenergetics, vol. 6, pp. 393-403 (1979).
Terabe, S., Anal. Chem., vol. 76, pp. 240A-246A (2004).
Torchilin and Weissig, Liposomes. A Practical Approach, 2nd Ed., Oxford Univ. Press, Oxford UK, pp. 3-29 (2004).
Valtchev & Mintova, Zeolites, "The effect of the metal substrate composition on the crystallization of zeolite coatings," vol. 15, pp. 171-175 (1995).
Van de Kant et al., Histochem. J., vol. 20, pp. 335-340 (1988).
Van den Brink et al., Histochem. J., vol. 22, pp. 327-334 (1990).
Varma, R. "Microwave Accelerated Solvent-Free Chemical Reactions," AMPERE Newsletter, Issue 29, ISSN 1361-8598; pp. 3-4 (2001).
Wathey et al., "The impact of microwave-assisted organic chemistry on drug discovery," Drug Discovery Today, vol. 7, pp. 373-380 (2002).
Weise et al., "Increased Efficiency of Fluorescence In Situ Hybridization (FISH) Using the Microwave," Journal of Histochemistry and Cytochemistry. vol. 53, No. 10 pp. 1301-1303 (2005).
Wood, W.G., "Luminescence immunoassays: problems and possibilities," Journal of Clinical Chemistry and Clinical Biochemistry, vol. 22, pp. 905-918 (1984).
Xiang, X., "Combinatorial materials synthesis and high-throughput screening: An integrated materials chip approach to mapping phase diagrams and discovery and optimization of functional materials," Biotechnol. Bioeng., vol. 58, pp. 227-241 (1998).
Yamamoto et al., "Immobilization of a bio-catalyst (enzyme) on a ceramic surface treated by the SPCP-CVD method," Advanced Powder Technol., vol. 7, pp. 271-277 (1996).
Yang et al., "Heirarchically ordered oxides," Science, vol. 282, p. 2244 (1998).
Yu et al., "Enhanced coupling efficiency in solid-phase peptide synthesis by microwave irradiation," Journal of Organic Chemistry, vol. 57, pp. 4781-4784 (1992).
Zlotorzynski, A., "The application of microwave radiation to analytical and environmental chemistry," Critical Reviews in Analytical Chemistry, vol. 25, p. 43 (1995).
Zubritsky, E., "Spotting a microarray system," Modern Drug Discovery, pp. 59-71 (May 2001).

* cited by examiner

1. Dielectric Surface
2. Surface-bound reactants 1. reagent capture membrane (upper layer)

2. underlying inert support (optional middle layer)
3. dielectric layer (lower layer)

1. reagent capture membrane
2. underlying support (optional)

3. dielectric platform (instrument component)

1

2

3

4

5

6

METHODS AND COMPOSITIONS FOR DIRECTED MICROWAVE CHEMISTRY

CROSS-REFERENCE TO RELATED APPLICATIONS

This application is a divisional of U.S. Patent Application Ser. No. 10/842,512 (filed on May 11, 2004) now abandoned, which is a continuation-in-part of U.S. Patent Application Ser. No. 10/234,092 (filed on Sept. 5, 2002, now U.S. Patent No. 7,348,182), which application is a continuation-in-part of U.S. Patent Application Ser. No. 09/968,517 (filed on Oct. 2, 2001, now U.S. Patent No. 7,351,590), which application claims priority to U.S. Provisional Patent Application Ser. No. 60/237,192 (filed on Oct. 3, 2000, now abandoned), all of which applications are herein incorporated by reference in their entirety.

FIELD OF THE INVENTION

The present invention relates to the field of microwave chemistry. It also relates to the field of biotechnology, specifically microplate- and array chip-based preparative and analytical chemistry.

BACKGROUND OF THE INVENTION

Until now, no one has performed chemical transformations as disclosed herein. Devices are used that emit radiofrequency/microwave energy. The energy is directed to a target object, for example, a microarray chip or a microtiter plate that contains one or more material(s) that absorb(s) microwave energy. The microwave-generated heat energy accelerates a desired chemical reaction on or near the surface of the targeted object.

Microwave Chemistry

Microwaves (including radiofrequency or RF electromagnetic radiation) are commonly used in wireless communication devices. Advances in microwave transmission have improved along with tremendous recent technological improvements in the satellite and communications industry (for example, in cell phones and wireless internet).

Microwaves are also well known in common kitchen appliances. Microwave ovens heat water-containing food rapidly because water is efficient at converting microwave energy to thermal energy. Kitchen microwave ovens emit microwaves at a frequency of 2.45 GHz, which is well within the microwave absorption spectrum of water. Frequencies outside of the absorption spectrum of water would not heat food as well.

Another use for microwave heating is in chemical reaction applications (Bose et al., 1997; Bradley, 2001; Wathey et al., 2002; Lew et al., 2002). Microwave chemistry refers to the use of microwaves to accelerate chemical reactions. Reactions are usually carried out using microwave radiation to heat bulk solutions that contain the reactants (Mingos & Baghurst, 1991; Zlotorzynski, 1995). Often these reactions are performed in non-aqueous solvents. Microwave ovens specifically designed for use in carrying out microwave chemistry of bulk reaction solutions are commercially available (CEM Corporation (Mathews, N.C.), Milestone, Inc. (Monroe, Conn.), Personal Chemistry AB (Uppsala, Sweden), PerkinElmer Instruments (Shelton, Conn.)).

Microwave accelerated reactions are sometimes run on solvent-free supports such as alumina and silica (Varma, 2001; Bose, 1997; Bram et al., 1990). The supports can be doped with reagents, for example in detoxifying waste. The supports are chosen because they are inexpensive and recyclable agents which non-specifically adsorb/extract the reagent of interest. No specific binding, such as by antibodies or nucleic acids, is used to capture reagents.

Another example of the application of microwaves to accelerate chemical reactions is the use of microwave-absorbing particles to enhance the heating of a bulk solution (Holworth et al., 1998). In this case, dispersed cobalt and magnetite nanoparticles were used as microwave (2.45 GHz) absorbers to heat a bulk xylene solution. Xylene is a non-polar solvent not appreciably heated by microwaves at 2.45 GHz. In one such case, microwaves were used to accelerate the rate of an enzyme-catalyzed reaction (Kidwai et al., 1998). In another case, Milestone, Inc. (Monroe, Conn.) sells microwave-absorbing/heating composites of PTFE and graphite which are designed to be dropped into test tubes to accelerate microwave heating of solutions during chemical syntheses. However, in these cases the microwaves are not directed to heat a surface, but used to heat the bulk solution.

In another application, microwaves have been used to heat the bulk solvent during solid-phase combinatorial chemistry (Kappe, 2001; Bradley, 2001; Lidstrom et al., 2001; Blackwell, 2003). In these cases, conventional resins (polystyrene, for example) function as solid scaffolds for chemistry. The bulk solution was the target of the microwave heating.

In another case, microwaves were used to accelerate a chromogenic reaction between noble metals and chromogenic reagents. This analytical reaction was performed in solution by flow injection analysis (FIA) (Jin et al., 1999). The reaction depended on bulk solvent heating rather than targeted dielectric material heating.

In yet another case, microwaves were used to enhance the solution phase formation of a fluorescent complex of aluminum (Kubrakova, 2000). The fluorescence intensity could be used to measure aluminum ions in solution. Again, the reaction depended on bulk heating of solvent.

In yet other cases, microwave heating has been used in biochemistry applications. Microwave heating has been used to assisted in protein staining (Nesatyy et al., 2002; Jain, 2002). Bulk microwave heating of samples has been used to accelerate antibody-antigen binding reactions in immunoassays, immunohistochemical assays, and DNA in-situ hybridization assays (Leong & Milios, 1986; Hjerpe et al., 1988; van den Kant et al., 1988; Boon & Kok, 1989; Kok & Boon, 1990; van den Brink et al., 1990; Slap 2003). In another example, microwaves were used to accelerate the enzymatic synthesis of oligosaccharides (Maugard et al., 2003). In another instance, microwaves were used as a heat source during PCR (Fermer et al., 2003). In none of these instances was microwave heating directed to a solid surface, but rather microwave heating was applied to heat a bulk aqueous target.

The present invention discloses a novel means of using microwave energy to accelerate specific chemical reactions on or near a microwave susceptible material. Reaction specificity comes from the fact that the reactants (or molecules that form the reactants) are biomolecules capable of biospecific interactions. Microwave irradiation causes a temperature increase in the microwave susceptible material, which consequently causes a reaction rate increase of the reactants to form products.

OBJECTS OF THE INVENTION

The invention is directed toward an improved process and apparatus for accelerating the rate of specific chemical reactions. It is another objective of the invention that the accelerated reactions be highly controllable, so that they can be selectively turned on or off, or be modulated, by a user at will. It is yet another objective of this invention to efficiently direct microwave heating to the surfaces of bioanalytical array chips and microtiter plates to accelerate preparative and analytical reactions. A further objective of the invention is to provide such improved reaction rates and specificity to a diverse number and type of analytical and preparative chemical reactions. It is yet another objective of this invention to accelerate biospecific binding interactions, such antibody-antigen binding and hybridization of nucleic acids. It is yet another objective of this invention to perform polymerase chain reaction (PCR) amplification of nucleic acids.

SUMMARY OF THE INVENTION

Figure 1A:
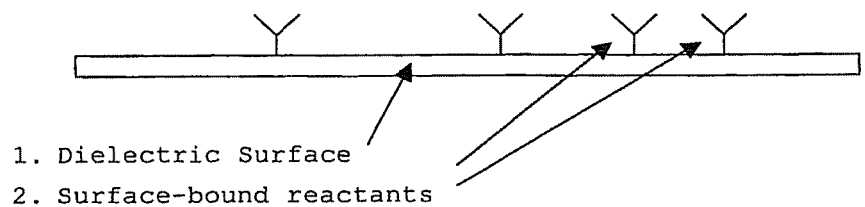
FIG. 1a-1c: Planar surfaces for directed microwave chemistry (e.g., on a microarray chip or in the well of a microtiter plate). The surface on which the reaction occurs may contain the dielectric as shown in FIG. 1a or be adjacent to the dielectric, as shown in FIG. 1b and FIG. 1c. The dielectric can be a part of a disposable reaction cartridge (e.g., part of an array chip or microtiter plate) as in FIGS. 1a and 1b, or the dielectric may be a permanent part of the microwave-generating instrument as in FIG. 1c.

The invention describes a means in which chemical reactions (catalytic or stoichiometric) can be accelerated by targeted microwaves. The invention has been given the acronym "MATTR", which stands for Microwave Accelerated Targeted Triggered Reactions. The reactions preferably occur on or near solid surfaces (hereinafter collectively referred to as "solid supports"). Suitable solid supports contain a microwave absorbing material, which heats upon absorbing microwaves. Reactants may be covalently or non-covalently attached to the surface, or they may be within thermal proximity of the microwave absorber, but not attached to the surface. For example, the reactants may be on the surface of a microchip or in the well of microtiter plates used for bioanalytical reactions. The microwave instrument power, frequency, and duration of the microwave emission are predetermined in the laboratory. Following microwave heating, a change in the reagent may be noted by a physico-chemical change that takes place in the formation of product(s) from reactant(s). The specific chemical rate acceleration can be used for preparative and/or analytical applications. In analytical applications, the reaction may optionally be monitored and/or quantitated, for example in medical diagnostics, by an accompanied observable physico-chemical change (color change, for example). In preparative applications, the presence of a microwave-dielectric layer can assist in surface chemistry to prepare the solid support for subsequent analytical reactions or be used to accelerate heat-dependent molecular binding and amplification reactions.

In detail, the invention provides a method for accelerating a chemical reaction involving one or more reactant(s) and a carrier fluid, the method comprising:
  (a) providing a composite material to the reactant(s) and carrier fluid, the composite material comprising a solid material susceptible to dielectric heating,
  (b) applying an electromagnetic field to the composite material, the electromagnetic field being sufficient to result in dielectric heating of the solid material, and
  (c) allowing the composite material to transfer heat to the reactant(s);
  (d) whereby product is formed from the reactant(s), thereby accelerating the chemical reaction.

The invention further concerns the embodiments of such method wherein the chemical reaction comprises a biospecific binding reaction.

The invention further concerns the embodiments of such methods wherein one or more the reactant(s) is a protein molecule, or an antibody or a fragment of an antibody that retains the biospecific binding specificity of the antibody or a nucleic acid molecule.

The invention further concerns the embodiments of such methods wherein the chemical reaction is between an antibody and its antigen.

The invention further concerns the embodiments of such methods wherein the reaction comprises annealing two nucleic acid molecules to one another. The invention further concerns the embodiments of such methods wherein the chemical reaction comprises a nucleic acid amplification reaction (especially a polymerase chain reaction).

The invention further concerns the embodiments of such methods further comprising the step of measuring the extent or rate of the chemical reaction.

The invention further concerns the embodiments of such methods further comprising the steps of:
  (e) contacting the composite with one or more reactant(s) capable of participating in a biospecific interaction with a reactant (a), or a product produced as a consequence of a chemical reaction involving a reactant (a),
  (f) allowing the additional reactant(s) to react in the biospecific interaction, and (g) measuring the extent or rate of the biospecific interaction.

The invention further concerns the embodiments of such methods further comprising the acceleration of one or more additional reactions, the method comprising the additional steps of:

(e) contacting the composite with one or more additional reactant(s), wherein the reactant(s) are capable of participating in one or more further chemical reactions involving a reactant (a), or a product produced as a consequence of a chemical reaction involving a reactant (a), (f) applying an electromagnetic field to the composite, the electromagnetic field being sufficient to result in dielectric heating of the solid material, the additional reactant(s) being heated by heat transfer from the heated solid material, and (g) allowing the heated additional reactant(s) to react with either a reactant (a), or a product produced as a consequence of a chemical reaction involving a reactant (a), thereby accelerating the one or more additional chemical reactions.

The invention further concerns the embodiments of such methods further comprising the step of measuring the extent or rate of the chemical reaction.

The invention further concerns the embodiments of such methods wherein the one or more additional reaction(s) comprises the annealing of two nucleic acid molecules. The invention further concerns the embodiments of such methods wherein such one or more additional reaction(s) comprises a nucleic acid amplification reaction (especially a polymerase chain reaction (PCR).

The invention further concerns the embodiments of such methods wherein the wavelength of the applied field is between 1 cm and 100 m.

The invention further concerns a composite comprising a solid material responsive to dielectric heating having a surface molecule capable of biospecific interaction with a reactant molecule.

The invention further concerns the embodiments of such composite wherein the surface molecule is bound or immobilized to the surface via a noncovalent adsorption reaction.

The invention further concerns the embodiments of such composite wherein the surface is capable of a covalent conjugation reaction with the reactant molecule.

The invention further concerns the embodiments of such composite wherein the surface is selected from the group consisting of a microarray chip, a macroarray chip, a test tube, a Petri dish, and a microtiter plate.

The invention further concerns an instrument that emits electromagnetic radiation sufficient to accelerate a chemical reaction, wherein the chemical reaction involves (a) providing a composite material to the reactant(s) and carrier fluid, the composite material comprising a solid material susceptible to dielectric heating, (b) applying an electromagnetic field to the composite material, the electromagnetic field being sufficient to result in dielectric heating of the solid material, and (c) allowing the composite material to transfer heat to the reactant(s);

(d) whereby product is formed from the reactant(s), thereby accelerating the chemical reaction.

The invention further concerns the embodiments of such instrument wherein the chemical reaction comprises the annealing of two nucleic acid molecules.

Definitions

Accelerate: To increase the rate of a chemical reaction, preferably by at least 10%, more preferably by at least 50%, and most preferably by at least 100% or more.

Aqueous Solution: A liquid medium that is more than 50% water by volume.

Biospecific Binding Reaction (Biospecific Interaction): The contact of a biological molecule to a biological or non-biological molecule via three or more spatially distinct physical interactions. The interactions are typically van der Waals interactions, hydrogen bonds, and ionic interactions. Biospecific interactions may also involve covalent bonds.

Cartridge: A vessel or device in which a reaction takes place. The cartridge may be coated with a dielectric. Examples of cartridges are microarray chips and microtiter plates.

Chemical Reaction: The chemical transformation of one or more molecules (reactant(s)) to form one or more molecules (product(s)). The definition includes covalent (such as hydrolysis) and noncovalent (such as binding events) transformations.

Chip: An essentially planar object that has one or more zones on its surface for desired chemical reactions to take place. A chip is preferably small enough and light enough to be held in one hand. If biological molecules are involved in the reactions, the chip is also known as a biochip.

Composite: A solid made of two or more distinct types of materials or molecules. If a composite is made of multiple materials, the materials may be blended or physically distinct. If physically distinct, the materials may be irreversibly joined (e.g., glued together) or reversibly joined (e.g., snapped together).

DNA: Deoxyribonucleic acid, usually 2'-deoxy-5'-ribonucleic acid. The sequence of nucleotide residues of DNA can comprise genes that can encode proteins. Cells possess the capability to read this code to form proteins.

Dielectric Heating: Heating of a dielectric (electrically-insulating) material by electromagnetic radiation in the wavelengths between approximately 5 cm and 100 m.

Hybridization: Coming together (annealing) of single-stranded nucleic acid sequences by hydrogen bonding of complementary bases to form double-stranded molecules; this process is the basis for molecular biological techniques in which a labeled probe oligonucleotide is used to detect a polynucleotide or oligonucleotide possessing the identical or similar sequence (e.g., Southern hybridization, Northern hybridization). Hybridization is also critical in PCR amplification of nucleic acids.

Lossy Material: A (dielectric) material that loses absorbed microwave energy in the form of heat.

Macroarray: A panel of a plurality of reaction zones on a chip ranging from 1 to 1000 zones.

MATTR: "Microwave-Accelerated Targeted Triggered Reaction" technology.

Microarray: A panel of reaction zones on a chip numbering greater than 1000.

Microtiter plate: An object commonly used in biomedical laboratories containing an array of multiple reaction wells. Typically, microtiter plates are disposable, made of clear acrylic, and have 24 (arranged in a 4×6 array), 96 (8×12 array), 384 (16×24 array), or 1536 (32×48 array) wells.

Microwave: Electromagnetic radiation in the range of $3 \times 10^2$ to $3 \times 10^4$ MHz (wavelengths of 1 m to 1 cm). Dielectric heating occurs in this range, but also occurs at longer (radio) wavelengths (up to 100 m), which could be alternatively used. Overall, microwave heating (herein defined to include radiofrequency dielectric heating) frequencies span wavelengths of about 1 cm to 100 m.

Microwave Oven: A device that emits microwave radiation at a pre-determined wavelength into an internal chamber. The chamber is typically closed to limit the escape of microwaves.

Molecular Imprinting: A process whereby specific binding sites to a chosen target (imprint) molecule are introduced into synthetic materials. The binding material is usually an organic polymer. Typically, functional and cross-linking monomers are co-polymerized in the presence of the imprint molecule, which acts as a molecular template. Subsequent removal of the template molecule reveals binding sites that are complementary in shape and size to the imprint molecule. In this way, molecular memory is introduced into the polymer, enabling it to re-bind the imprint molecule with high specificity.

Nucleic Acid: A large polymer molecule composed of nucleotide monomers.

Organic Solution: A liquid medium that is more than 50% organic solvent by volume.

Oligonucleotide: A nucleic acid molecule having 99 or fewer nucleotide residues.

Polymerase Chain Reaction (PCR): A method for amplifying specific DNA segments. The method amplifies specific DNA segments by cycles of template denaturation; primer addition; primer annealing and replication using thermostable DNA polymerase. The degree of amplification achieved is a theoretical maximum of $2^N$, where N is the number of cycles, e.g. 20 cycles gives a theoretical 1,048,576-fold amplification (see, U.S. Pat. Nos. 4,683,195 and 4,683,202).

Polynucleotide: A nucleic acid molecule having more than 99 nucleotide residues.

Porous: A solid material containing channels through which water and other liquid molecules can pass.

RNA: A usually single-stranded nucleic acid similar to DNA but having ribose sugar rather than deoxyribose sugar and uracil rather than thymine as one of the pyrimidine bases.

Thermal Proximity: The situation in which one substance is close enough to a second substance to permit substantial heat transfer to occur between them.

Thermocouple: A sensor for measuring temperature consisting of two dissimilar metals, joined together at one end. The metals produce a small unique voltage at a given temperature. The voltage is measured and interpreted by a thermocouple thermometer.

Waveguide: A structure that causes a wave to propagate in a chosen direction. It is accomplished by an intimate connection between the waves and the currents and charges on the boundaries, or by some condition of reflection at the boundary.

DETAILED DESCRIPTION OF THE PREFERRED EMBODIMENTS

Directed Microwave Heating

Dielectric materials are good at absorbing microwaves. Dielectrics have unique spectral characteristics of frequency versus heating ability, with different substances heating more effectively at different frequencies (Gabriel et al., 1998). Although dielectric heating is referred to here as microwave heating, dielectric heating can also occur at radio frequencies. This invention is intended to include those effects.

Dielectric heating depends on a number of factors including the frequency of the microwave irradiation and the absorption properties of the dielectric at that frequency. All dielectric materials have characteristic absorption spectra (frequency vs. heating ability). For example, in a conventional kitchen microwave oven, the microwave frequency (2.45 GHz) is very good for heating water, but not good for heating other materials (for example, a cup that holds the water). If the frequency of the microwave emission would be changed, in theory one could heat the cup but not the water (depending on the relative dielectric absorption characteristics of water and the cup).

In this invention, microwaves heat materials that are especially good at absorbing microwaves. The microwave-active materials are in thermal proximity to biological molecules. Heat from the microwaved materials accelerate reactions associated with the biological molecules to give a rapid desired result, such as a biological binding event or a signal indicated the presence of an unknown biomolecule. Thus, heating of the biological molecules (and subsequent accelerated chemistry) is targeted by microwave heating because they are close to the microwave-susceptible material.

The invention has several advantages over other heating methods. These alternative methods include IR heating (using a lamp) and resistive heating. Resistive heating requires direct contact of the reaction surface with an electrical circuit and resistor, while the present invention obviates the need for direct contact. IR heating, although non-contact, is less efficient in rapidly heating a surface than is microwave heating. Also, some reactants are photosensitive and damaged by IR light. Finally, although it is extremely difficult to shine a IR light beam in a sharp pattern, the present invention allows patterned microwave absorption by high resolution patterning of microwave-absorbing dielectrics.

Physical Components of a Preferred Embodiment of the Invention:

The physical components of a preferred embodiment of the invention are:

1) The instrument. The instrument (illustrated by reference to a preferred embodiment shown in FIG. 2) contains; (a) a microwave source and (b) one or more reaction chamber(s). The instrument also optionally contains; (c) a means of controlling the reaction temperature in real time and (d) one or more detection system(s) to measure physiochemical changes in the sample (e.g., light emission and temperature). Each of these will be considered separately here.

a. Microwave source. Microwaves can be generated by various devices including a magnetron, a solid-state device (such as a Bluetooth or Wi-Fi (IEEE 811.b)), a klystron, a cross-field amplifier, a traveling wave tube, a backward-wave oscillator, or any combination thereof. The microwave emission is in the frequency range of 300 to 30,000 MHz (wavelengths of 1 m to 1 cm). Dielectric heating also occurs at lower (radio) frequencies of down to 3 MHz (wavelengths of up to 100 m), which can be alternatively used. Overall, microwave/dielectric heating frequencies span wavelengths of about 1 cm to 100 m. Electromagnetic heating throughout this range is considered part of this invention. The ideal frequency used depends on factors including the identity of the dielectric material to be heated. As described above, there are many devices that generate microwaves—most notable for the present invention are magnetrons and solid-state devices. Low power magnetrons (500-1200 W) commonly found in kitchen microwave ovens are sufficient for the invention. Alternatively, solid-state devices, such as Bluetooth or Wi-Fi chips, are commonly used in wireless communication devices. They emit low power (<1 W) microwaves at the same frequency as kitchen microwave ovens (2.45

GHz). These devices, which are roughly the size of a house key, are much smaller than light-bulb-sized magnetrons. Hence, solid-state devices can generate microwave power in a handheld device. The low power levels are sufficient for use in this invention, especially if the dielectric heats well and if the sample to be heated is placed in a waveguide (see below).

Attractive frequencies for this invention include 0.915 GHz, 2.45 GHz, 5.85 GHz, and 22.125 GHz. The U.S. Government currently approves these frequencies for use for industrial, scientific, and medical uses (Boon & Kok, 1989). Other frequencies may also be attractive provided that the emission within the microwave chamber is sufficiently shielded (to prevent interference with communications uses of microwaves). Of the above-listed frequencies, 2.45 GHz is attractive because it is a widely accepted frequency used in numerous existing devices such as domestic microwave ovens and many wireless communications devices (Wi-Fi and Bluetooth). Because of widespread use of these devices, design and manufacturing know-how of 2.45 GHz emitters including magnetrons and solid-state devices are well known. A frequency of 0.915 GHz is also an attractive frequency for aqueous applications because water is least susceptible to dielectric heating at this frequency (Laslo, 1980).

b. Reaction chamber. The reactions may be carried out within an open cavity, such as a microwave oven or a waveguide. Both microwave ovens and waveguides are well known in the art and readily adaptable to directed microwave chemistry.

In the case of an oven cavity, it is preferable for the microwaves to be "homogenized" to prevent uneven heating/reactivity. This can be accomplished through the use of a rotating sample carousel or through the use of irregularities or deflectors in the oven, which would mix the microwaves.

A preferable chamber would be a waveguide (for example, sold by Coleman Microwave Company (Edinburg, Va.) and Gerling Applied Engineering, Inc., Modesto, Calif.). Microwaves within a waveguide are very uniform. Moreover, the interior of a waveguide is small which can be readily used with correspondingly small chips and plates. One or more holes can be introduced into the waveguide for practical purposes, such as a slot for plate or chip insertion and an orifice for light or temperature measurement. Waveguides are widely available commercially and can also be custom designed based on known microwave algorithms.

The dielectric, which is targeted by microwaves, may either be permanently incorporated into the wall of the reaction chamber or be a part of the disposable sample support (e.g., a microarray chip or microtiter plate). In the former case, the sample (a conventional chip or plate) would be placed on the dielectric in the reactor chamber. In the later case, the chip or plate would be modified to include a dielectric layer.

An alternative reaction chamber to those described above is one that is outside of a microwave oven or waveguide, yet abuts a microwave chamber. When this type of reaction chamber is used, the sample would heat, but not come in direct contact with microwave irradiation. The sample would be placed in contact with a dielectric material that is physically built into the wall of the waveguide/oven cavity. The wall dielectric would heat from the interior microwave bath, and heat from the dielectric would thermally transfer to the outside surface where it would contact the sample. The advantage of this format is that microwaves would not directly contact the sample to be heated. Thus, materials incompatible with microwaves could be more easily used. For example, a metal thermocouple used to measure sample temperature might spark on the inside of a microwave oven.

c. Temperature Controller. It is generally desirable to control the reaction temperature in real time. A thermocouple can be used to measure the temperature of the dielectric provided that the dielectric is structurally amenable (for example a chip-based dielectric. One example is if the dielectric is coated on a disposable chip (i.e., a microscope slide). A thermocouple could be used to contact the chip and monitor the temperature during heating. Moreover, thermocouple temperature measurement could be used to control the temperature by controlling the power of the microwave oven. If the dielectric temperature reached a certain level, say 95° C., the microwave could be automatically shut off. When the temperature dropped, to say 77° C., the thermocouple would cause the microwave to begin heating again. Such thermocouple-based temperature control is well known art (Huhmer and Landers, 2000; ASTM, 1993; Kreider, 1989). Alternatively, temperature can be measured using non-contact spectroscopic techniques (Boon & Kok, 1989; Slyanev et al., 2001). Both thermocouples and spectroscopic methods have been used to measure microchip temperatures (Huhmer and Landers, 2000; Slyanev et al. 2001).

d. Detection System(s). Detection is an attractive (but non-essential) embodiment of this invention. Detection may be by a number of means such as fluorescence, absorbance, or chemiluminescence. In accordance with the principles of preferred embodiments of the present invention, surface-directed microwave heating can preferentially enhance numerous chemical reactions, including reactions that are accompanied by measurable physicochemical changes, such as chemiluminescence. These observable reactions are useful in microwave-based molecular analyses. For analytical applications, the reaction will be chosen depending on the preferred detection method (a change in color, luminescence, etc.). The detector is positioned opposing the reaction, for example on a microtiter plate. It may be within the reaction chamber, but will preferably not interfere with reaction. For example, if light emission or transmission is to be measured, a suitable detector (PMT, CCD camera, human eye, film, or photodiode array) will be positioned to read signal. In some cases, such as fluorescence and UV absorbance, the microwave induced physicochemical change might only be observable upon external excitation. In these cases, the instrument would require both an excitation source and a detector. Examples of common excitation sources are lasers, tungsten lamps, and white light bulbs.

2) The Microwave-Absorbing Material. Numerous solid materials absorb microwaves and consequently heat rapidly. These materials are either pure or composites with other materials, such as silicone or plastics. There are many materials that could work in this invention to absorb microwaves and heat such that the heat is transferred to accelerate a chemical or biochemical reaction.

One material with a high dielectric constant is barium titanate ($BaTiO_3$). The dielectric constant is 200-16,000

(compared with 80 for water). Barium titanate can be formed into films and has been used in analytical devices (Ewart et al, U.S. Pat. No. 5,922,537). Moreover, in addition to barium titanate, methods for forming thin and thick films of other ferroelectric materials at low temperature have improved steadily. Known high dielectric constant inorganic titanates, niobates, and ferroelectric polymers can be formed by many processes including low temperature chemical vapor deposition, laser photo-ablation deposition, sol-gel processes, RF magnetron sputtering, screen printing and firing, (in the case of the polymer) spin coating, and other methods (Yang et al., 1998).

Natural clay can also be used as a moldable dielectric. In addition, a 1:1 w/w mixture of alumina-magnetite ($Al_2O_3$—$Fe_3O_4$) can be used as a dielectric support that heats strongly (Bram et al., 1991). Magnetite ($Fe_3O_4$) particles heat well under microwave irradiation.

Another material that could be used is carbon. Forms of carbon include carbon black, activated charcoal, graphite, carbon nanotubes and nanospheres (such as $C_{60}$ and $C_{70}$).

Many additional dielectric materials can be identified by screening dielectrics for their ability to heat during microwave irradiation. Class I dielectrics (dielectric constants typically less than 150) and Class II dielectrics (dielectric constants typically in the range of 600-18,000) can be used (technical brochure, Novacap, Inc., Valencia Calif.). Other suitable materials include organic polymers, aluminum-epoxy composites, and silicon oxides. The microwave frequency can be varied as well. This simple screening procedure would yield conditions (frequency and material) that would direct heating toward the dielectric material.

Still other materials that heat substantially under RF irradiation include ferrites and ferroelectrics. In addition to $BaTiO_3$, described above, other Perovskites (minerals of the chemistry $ABX_3$) such as $NaNbO_3$, $LaCoO_3$, $LaSrO_3$, $LaMnO_3$, and $LaFeO_3$ heat well in a microwave field. Other materials that heat efficiently in a microwave and which could be used in the invention include SiC, AlN, ZnO, MgO—SiC, $Al_2O_3$, and AlN—SiC.

Other types of materials that are well known to heat dramatically under microwave irradiation are various ceramics; oxides ($Al_2O_3$, for example), non-oxides (CrB and $Fe_2B$, for example), and composites ($SiC/SiO_2$, for example). Numerous materials are processed (sintered, etc.) by exploiting their microwave heating characteristics.

Microwaves can heat composite materials. For example, materials that are normally transparent to microwaves can be heated by adding polar liquids or conducting particles. Refractory oxides such as alumina, mullite, zircon, MgO, or $Si_3N_4$ have been made to couple effectively with microwaves by the addition of electroconductive particles of SiC, Si, Mg, FeSi, and $Cr_2O_3$. Oxides including $Al_2O_3$, $SiO_2$, and MgO have been effectively heated by the addition of lossy materials such as $Fe_3O_4$, $MnO_2$, NiO, and calcium aluminate. Indium tin oxide (ITO) could also be used. Mixtures of conducting powders, such as Nb, TaC, SiC, $MoSi_2$, Cu, and Fe, and insulators such as $ZrO_2$, $Y_2O_3$, and $Al_2O_3$, have coupled well with microwaves. Various materials in solution (zirconium oxynitrate, aluminum nitrate, and yttrium nitrate) that are good couplers have also been added to enhance microwave absorption of powdered insulating oxides. A microwave absorbing heating mantle is sold by Milestone, Inc. made from a composite of graphitic carbon and Teflon. Microwave-absorbing materials are also sold by Emerson & Cuming Microwave Products, Inc. (Randolph, Mass.). These include ECCOSORB®, which are made from microwave-absorbing materials (carbon, iron, magnetically, or ferrite loaded) composited in a polymeric matrix such as silicone, vinyl or polyurethane. ECCOSORB® can be purchased in sheets of various sizes and thicknesses, with or without adhesive backing.

Addition of conductive materials in various shapes including powder, flake, sphere, needle, chip, or fiber, would cause the heating of low loss materials. For example carbon black or metal pieces with sizes ranging from 0.1-100 μm can increase the heating properties when used as inclusions. The nature and concentration of such materials can be optimized without undue experimentation (Committee on Microwave Processing of Materials et al., 1994).

The microwave-absorbing material can be an integral part of the microwave-generating instrument, or it can be an accessory thereof. In this case, the material would be situated in thermal proximity to the reaction surface. Alternatively, the microwave absorber can be incorporated into or applied to the bottom of a disposable reaction vessel such as a microarray chip of 96-well plate. Numerous application methods are available including painting (as an ink, such as carbon ink, or in a binder such as aqueous polyvinyl acetate (PVAc), screen printing (such as SIC in terpineol), or by adhesive attachment of a polymer composite (such as ECCOSORB®, Emerson & Cuming).

3) The Chemical Reaction. In the broadest terms, the reaction can be any organic or inorganic reaction that is accelerated by heat. The reaction will either be: (1) a reaction that involves biospecific binding or, (2) a reaction that is part of a sequence of reactions, one of which is a biospecific reaction. The biospecific reaction typically involves a protein or nucleic acid molecule (e.g., enzyme, antibody-antigen, and nucleic acid-hybridization reactions). An example of a sequential reaction involving a biospecific interaction is enzyme catalysis to form a product, which then further reacts to form a second product. Another example of a sequential reaction is peptide synthesis followed by antibody binding to the synthesized peptide.

The biospecific binding molecule can be any molecule that is capable of specifically interacting the reagent(s). The molecule may be low or high molecule weight, natural or synthetic. Typical binding molecules could be antibodies, enzymes, receptors, nucleic acids, molecularly imprinted polymers, and zeolites. These molecules have specific binding pockets or crevices.

Reactions run without a bulk solution are useful in analytical applications (for example in medical diagnostics). In diagnostics, the reactant solution might contain a biological fluid from a patient. Microwaves may facilitate the capture and detection of a molecule of interest.

The following shows typical directed microwave reactions covered by this invention:
  i. Preparative Reactions
    1. Non-specific adsorption (e.g., a protein binding to plastic)
    2. Small molecule synthesis (e.g., peptide combinatorial chemistry)
  ii. Binding Reactions
    1. Biospecific Protein Binding
      a. Immunoassays
      b. Receptor-Peptide Binding
    2. Biospecific Nucleic Acid Hybridization
      a. PCR
      b. RNA detection
  iii. Analytical Reactions
    1. Chemiluminescent
    2. Fluorescent
    3. Colorimetric
  iv. Post-Analysis Heat Decontamination
4) Formats of Reactions. The support may have any of a variety of geometries. It may be a planar surface. A suitable planar dielectric may be part of a chip, such as a multianalyte disposable biological assay chip (protein chip or DNA chip) or part of a microtiter plate. Such apparatus may commonly either possess the dielectric material as one or more spots on their surface, or may comprise a continuous layer. Alternatively, the dielectric material could be in suspension in the form of a particle, such as a bead or quantum dot. Similar use of dielectric material can be used in reaction vessels commonly used in biology such as microarray chips/slides, microtiter plates, test tubes, Petri dishes, and centrifuge tubes.

Microtiter plates are in common use to perform biological analyses (Johnson, 1999). They typically have 96 wells in an 8×12 array, but can also have other configurations and numbers of wells including 24, 384, and 1536. They are (usually) disposable devices made of acrylic or polycarbonate, but can be made of essentially any material. The volumes of the wells vary depending on the number of wells per plate, but 96-well plate wells hold roughly 150 microliters of liquid. Immunoassays including ELISAs, enzyme assays, and nucleic acid assays are commonly performed in wells. Most often, a different assay is performed in each well (1:1), although it is becoming increasingly common via low-volume reagent spotting technologies (e.g., Cartesian Technologies, Inc. (Irvine, Calif.), BioDot, Inc. (Irvine, Calif.)) for multiple assays to be carried out in a single well. Typically, plates are prepared for analysis by coating the interior surface of the wells (entirely or by array spotting) with a specific capture molecule, such as an antibody. Binding usually occurs by non-specific absorption. Because binding is a surface phenomenon and bulk heating may denature biomolecules in the aqueous solution of the wells, it is preferable to target heating to the well surfaces. This can be done by microwave heating microtiter plates that have dielectric in thermal proximity to the well surfaces. This can be accomplished by coating the plate bottoms with dielectric, for example by painting, or by incorporating dielectric into the plate material (plastic).

Figure 7:
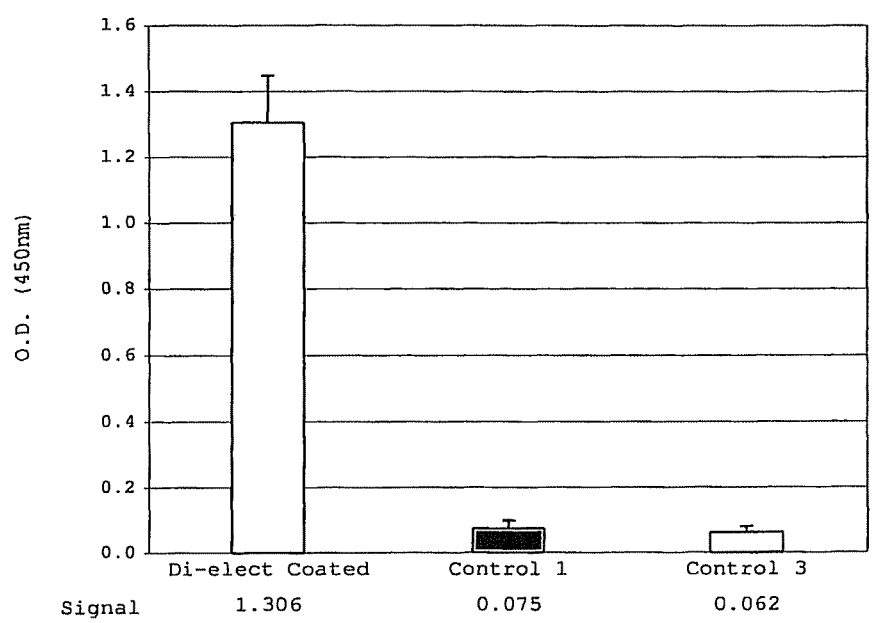
FIG. 7: Microwave-accelerated protein adsorption to microwell plates.

The effect of mild microwave heating on protein adsorption in a dielectric coated plate is shown in FIG. 7. The protein avidin was coated in 96-well plates (Nunc MaxiSorp) under varying incubation conditions. Plate-bound avidin was then detected using biotinylated horseradish peroxidase (HRP) as a label to generate color using the colorimetric HRP substrate, TMB. The height of the first column in FIG. 7 (Di-elect Coated) represents the relative amount of protein bound in a microwaved dielectric-coated ($BaTiO_3$) plate. The second column (Control 1) shows the relative amount of protein bound in a non-microwaved dielectric-coated plate. The third column (Control 3) represents the relative amount of protein bound in a microwaved non-dielectric-coated plate. These data show the importance of the dielectric coating to microwave-accelerated protein binding to plates.

Alternatively, conventional plates may be placed in a holder or mantle that contains dielectric material. In all cases, the dielectric is in thermal proximity to the surface where biomolecule attachment occurs. The extent of well coating can be measured by standard means known in the art, such as total protein or DNA determination using colorimetric or fluorescent reagents. Coating can also be analyzed by a function-based assay. Once the well is coated with the molecule of choice, an analytical reaction can occur (DNA probe assay, immunoassay).

There are three preferred ways in which the dielectric material can be in thermal proximity to the reaction surface. First, the dielectric can be incorporated into the material that makes up the solid support. For example, a composite of Teflon and graphite or barium titanate can be made (Milestone, Inc., Monroe, Conn.). Microarray chips or microtiter plates can be extruded or injection molded from the composite. Second, the dielectric can be attached or deposited as a coating or layer on the solid support. The dielectric can be painted or spotted to the underside of a chip or plate (for example, as a barium titanate or carbon paste). It can also be included within a chip as a "sandwich" layer. Third, the dielectric can be a solid mantle or holder on/into which the solid support is placed prior to reaction. In this third format, a chip or plate can be disposable but the dielectric mantle can be reused. A dielectric mantle also allows the dielectric material to have substantial mass (many grams), which facilitates rapid microwave heating.

Preferred Methods and Compositions of Matter

There are numerous ways of practicing the present invention. Some variables include: altering the microwave frequency and power, the identity of the microwave susceptible material, the reaction surface shape (planar or spherical), the reagent capture mechanism (antibodies, DNA, covalent, non-covalent, etc.), the identity of the reaction to be accelerated, and practical applications (analytical, bioanalytical, preparative, etc.). Described below is a brief overview of some variables and their practical application. Also described are the current best ways of carrying out the microwave accelerated targeted reactions.

One highly attractive format for the invention is to use it on "chips," i.e., disposable planar surfaces, often made on microscope slides (for example, 1×3 inch rectangles of glass). Another attractive format is to use it on "microtiter plates".

Many attractive potential uses of microwave-targeted reactions are in the fields of biotechnology/medicine. In these cases, measured analytes have biological function. Any conventional assay such as an immunoassay or a DNA probe assay can be carried out by the described technology. In these assays, well-known chemical conversions would occur causing a detectable physicochemical change in some label. For example, chromogenic, fluorogenic, or luminescent reactions could be carried out.

A spotting method may be used to deposit reagents. Spotting (commonly by inkjet printing, pipetting, pin contact or other high-resolution deposition methods) results in from one to thousands of reaction spots on the surface of a chip or one to several (e.g., a 4×4 array) spots within an individual microtiter plate well. There are numerous manual and automated means of spotting known in the art. Numerous commercial suppliers exist that sell spotting robots (Biodot, Cartesian) as well as simple inexpensive devices for spotting (Xenopore). Small volume analyses on such so-called "microchips" (Schmalzing et al., 2000) enable huge numbers of assays to be performed on a single chip. Arrays ("macroarrays" or "microarrays") on chips or in microtiter plates can be used for analytical purposes. Thousands of assays can be performed on a single chip or plate using deposition technologies know in the art, which are commercially widely available (Pasinetti, 2001; Lennon, 2000; Cooper, 2001; Draghici, 2001; Zubritsky, 2001).

A preferred way of conducting the procedure is to use composite dielectric materials containing SiC, carbon Emerson & Cuming), ferrite (Emerson & Cuming), or barium titanate-based materials. Carbon may be activated carbon/charcoal (Sigma-Aldrich Chemical Co.), carbon black (Columbia Chemicals, Marietta, Ga.; Reade Advanced Materials, Providence, R.I.), graphitized carbon particles (Polysciences, Inc. Warrington, Pa.). These materials can be printed or screen-printed onto the reaction device. Alternatively, dielectric-containing thin or thick films or sheets can be formed in advance and glued.

For example, an array of spots can be used to detect genetic mutations in a myriad of genes. Another example is an immunoassay, in which an antibody would be present in a spot. Another example is a ligand assay in which small molecule such as an alkaloid or a peptide would be present to capture a specific protein receptor. Chips and plates can be used in numerous analytical applications including but not limited to; biochemical research, human and animal medical diagnostics/prognostics, water testing, food pathogen testing, crop testing, and chemical/biological warfare agent testing.

In addition to analytical uses, surface-targeted microwave heating can be used preparatively. Extending the application of microchips and microtiter plates described above, the chips and plates could be prepared for subsequent analytical use using directed microwave reactions. One general area is the use of targeted microwave heating to enhance capture protein binding to plates or chips. Another general area is to use targeted microwave heating to accelerate on-chip or on-plate synthesis of small molecule compounds such as peptides or alkaloids. Another is accelerated biospecific binding involving proteins or nucleic acids. Another is microwave-targeted PCR.

In addition to preparative and analytical uses, the invention can be used for decontamination. If a sample being tested is pathogenic or toxic, such as an infectious agent or poison, microwave heating will inactivate the harmful effects. If the heat generated during analysis is insufficient for destruction, microwave power/time can be increased to facilitate sample decontamination.

Reactions of analytical utility include those that result in a change in color, luminescence, fluorescence, electrochemistry, or any other detectable physical property. Preparative reactions include hydrolysis, peptide or nucleic acid synthesis, and/or enantioselective reactions, etc. Any preparative reaction is potentially amenable to the described invention. As with analytical applications, preparative reactions can be monitored by changes in a detectable physical property.

Figure 3:
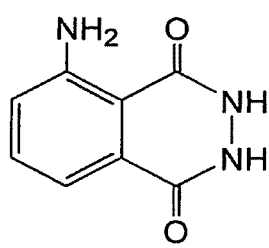
FIG. 3: Structures of MATTR Chemiluminescent Compounds.
Figure 3:
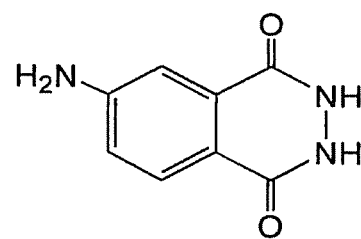
Figure 3:
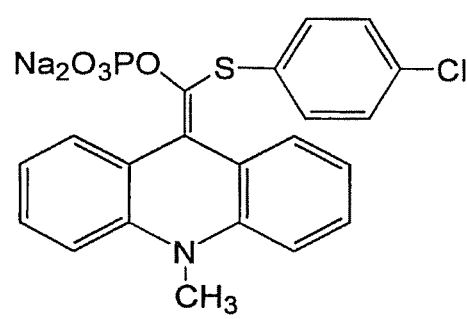
Figure 3:
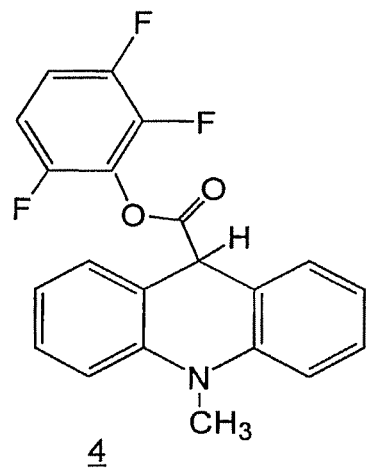
Figure 3:
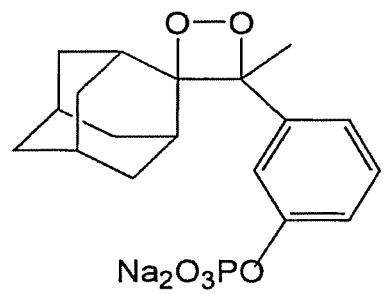
Figure 3:
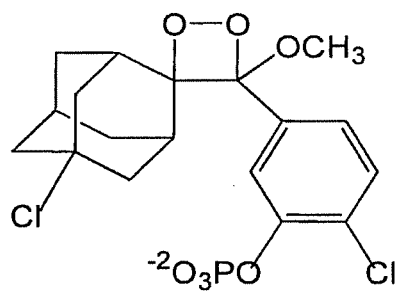

An attractive detection format is chemiluminescence (CL). These are described in greater detail below in the section delineating sample practical applications in medicine. Chemiluminescence reactions can be monitored and quantitated in many ways including the use of film (for example, X-ray film), or electronically using a photomultiplier tube (PMT) or a charge-couple device (CCD) camera. A PMT-based instrument would involve a microwave-emitting device with a window through which light is measured. Measurement using a PMT or a CCD camera would be collected and analyzed using a personal computer and conventional commercial data acquisition/analysis software (for example, LabVIEW). Numerous chemiluminescent reactions have been found to be useful in this invention (FIG. 3).

As described above, the dielectric material can be in various formats. Currently the most attractive format is on a chip, either as spots or as a layer. The use of a "dielectric chip" allows sensitive detection of multiple analytes. Indeed, microarray chips or microchips are an attractive application of the invention.

The size and features of the instrument will vary with the practical application. Some feasible types are handheld, portable, and benchtop.

Illustrative Preferred Embodiments

There are numerous practical applications of targeted triggered microwave reactions. Many are in the fields of analytical and preparative chemistry. Some though, are in non-analytical fields. For example, a reaction could be directed at a toxin (such as a nerve gas) to specifically inactivate that toxin. A capture step would preferably involve a material such as a molecularly imprinted polymer. The polymer would trap and concentrate the toxic gas. Directed microwave heating would then The described invention could be useful in any practical application where a chemical reaction is desired and it is important that that reaction is specific for the chosen molecule.

Very attractive applications are in the biomedical analysis. Analyses of biomolecules are critical to diagnostic/prognostic evaluations. Moreover, scientific research depends on the ability to detect and measure specific biomolecules. Such biomolecules include but are not limited to proteins (immunoassay detection) and nucleic acids (hybridization detection).

The herein described invention has numerous embodiments and applications that can be used alone or in series. For example, preparative, analytical, or decontamination uses could be used alone or in any combination. Examples include preparative, analytical, and decontamination embodiments used in series, or preparative and analytical embodiments, or analytical and decontamination embodiments. Thus, this invention can be viewed as modular.

MATTR Instrumentation in Biomedical Analyses

There are numerous feasible designs of instruments for MATTR. In essence, the instrument must be able to bathe the targeted dielectric in a uniform field of microwave irradiation. Instruments can be made with one or multiple reaction chambers. Instruments can also be different sizes, for example, a benchtop instrument can be made for laboratory use, while a handheld instrument can be made for field use. A MATTR instrument can be as small as the smallest microwave emitters combined with the smallest target reaction chamber. Microwave emitters can be smaller than a house key (e.g., in cell phones). Target reactions can also be smaller than a house key (e.g., a small microarray chip).

Figure 2:
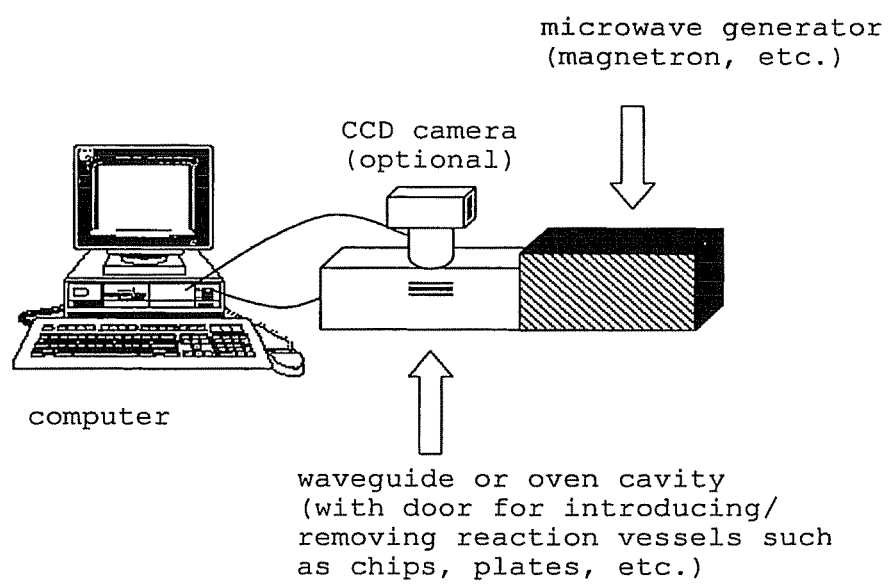
FIG. 2: A Microwave Accelerated Targeted Triggered Reaction ("MATTR") instrument. The components of the instrument are a microwave generator (such as a magnetron), a reaction cavity (e.g., oven or waveguide) with a built-in holder for MATTR disposable chips. The instrument may also include features such as temperature monitor (thermocouple or IR thermometer) and a light sensor such as a PMT or a CCD camera. Microwave generation (power, time, pulsing, etc.) can be controlled by computer. The computer can also be used to control/monitor temperature and record and analyze light acquisition.

Additional features are critical for some applications including real-time temperature monitoring/control and light emission measurement capabilities. The basic components of a MATTR instrument are shown in FIG. 2.

Experiments described in the Examples below were performed with a standard kitchen microwave oven. Equivalent or superior results can be expected using purpose-designed MATTR instruments. Two such designs are described below for illustrative purposes.

Figure 4:
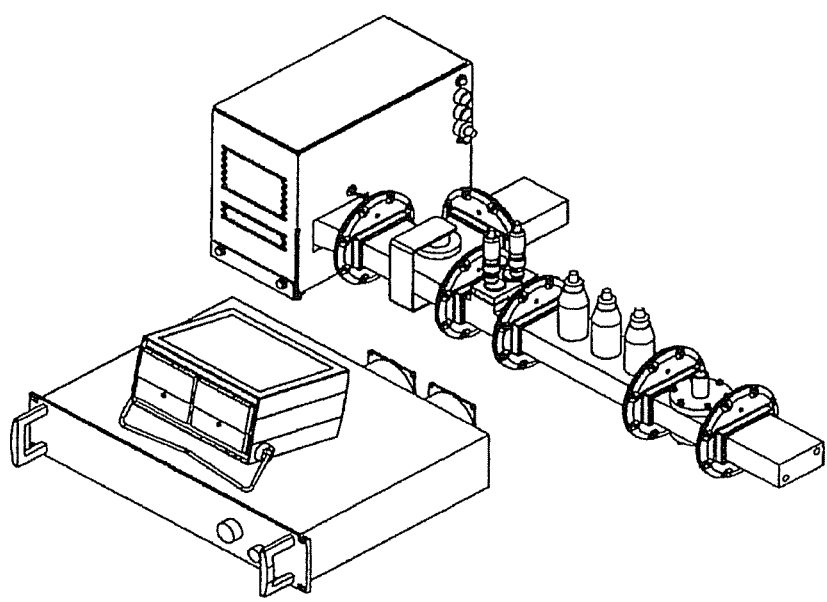
FIG. 4: Microwave components of a waveguide-based MATTR instrument. The figure includes the microwave generator and waveguide.
Figure 5:
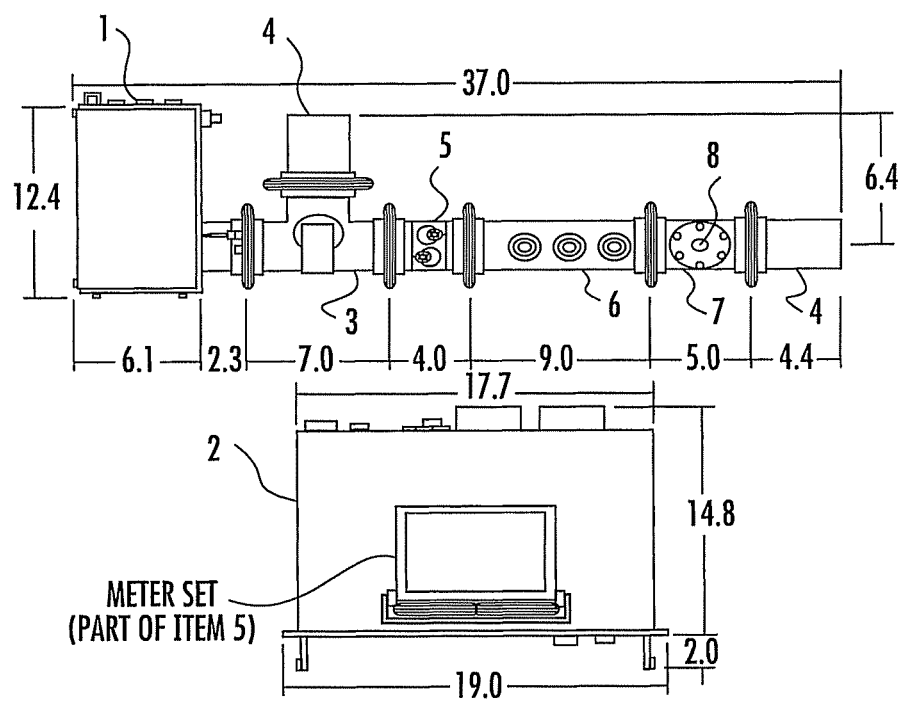
FIG. 5: Microwave components of the MATTR instrument shown in FIG. 4. The figure includes a close-up of the waveguide.

1) Waveguide-Based MATTR Instrument.
   a) Microwave Source and Chip Holder (FIGS. 4 & 5). The salient features of the system are as follows;
      i. The microwave source is a 1.2 kW magnetron generating 2.450 MHz microwaves.
      ii. The range of microwave power is 0.06-1.2 kW. The microwave source is controllable both manually and via LabVIEW 4.0 software (National Instruments, Inc.).
      iii. Perhaps the most important feature of the instrument is that the chips are irradiated in a waveguide, rather than in an oven cavity. A drawback of microwave ovens is that standing waves are generated in the oven cavity, resulting in uneven heating ("hotspots"). Hotspots do not occur within a waveguide because microwaves are uniform.
      iv. The waveguide in the instrument has an opening to give access to chips. When the chips are inserted, a 13 mm diameter aperture remains for observation of emitted light. The configuration of the aperture prohibits escape of microwaves. A PMT abuts the aperture. The PMT is held in place using a c-mount adaptor.

b) PMT Assembly. The PMT assembly is from Applied Scientific Instrumentation (Eugene, Oreg.). The assembly consists of a Hamamatsu H5784 series in a custom designed light-tight c-mount housing. The housing has a special optical collection element to maximize photon collection. The PMT has a power supply and control board offering manual and external control of gain.

c) Infrared Thermometer. Besides measuring light output, temperature is monitored with a non-contact infrared thermocouple thermometer (DigiSense Type J thermocouple). The surface temperatures of chips are read through the light aperture (the PMT is removed for temperature measurements). Because temperature readings are not sensitive to visible light, these measurements are performed manually without the need for light shielding precautions.

d) Computer and Software. A personal computer running LabVIEW 4.0 software is used to simultaneously control the microwave generator (power and duty mode (on/off timing)) and the PMT (gain, timing). LabVIEW is used to analyze the collected data.

FIGS. 4 and 5 illustrate the above-described microwave components. FIG. 4 shows the microwave components of a waveguide-based MATTR instrument. The two boxes in the unit at the lower left are a power supply and power monitor. The unit at the upper right is the microwave emission system, including the microwave source (magnetron, top) and waveguide containing the chip holder. FIG. 5 gives more details of the microwave components; (1) magnetron head, (2) switch mode power supply and power monitor, (3) 3-port circulator, (4) short 3 kW dummy load, (5) dual power monitor leads, (6) precision 3-stub tuner, (7) universal waveguide applicator, and (8) 13 mm test tube adaptor.

2) Oven-Based MATTR Instrument

The design of an oven-based instrument that uses fiber optics to detect emitted light is described here;

a) a suitable microwave oven is made from a microwave moisture/solids analyzer (model M2, Denver Instrument Co., Arvada, Colo.). The oven will has a single mode microwave chamber to provide a uniform power density. The microwave chamber of such an oven is small and cylindrical and the energy is focused on the sample. The operating frequency of microwave emission is 2450 MHz. The output power of the microwave is 550 W and the power source is 115 V, 60 Hz.

b) The interior of the oven chamber is fitted with a chip holder that is aligned with the fiber optic cables. The fiber optics is run from the interior of the microwave to a PMT on the exterior of the oven. The chip holder supports disposable dielectric assay chips of various sizes (for example, from 1×3 inches up to 5×5 inches).

c) A fiber optic detection system to allow chip imaging within the microwave chamber. Fiber optics leads from the chip to a light-recording photomultiplier tube (PMT, Hamamatsu model H5784-01), which captures light emitted light from the CL reaction, and d) a personal computer that controls and synchronizes the PMT and the microwave source. The computer runs a versatile data acquisition, control, analysis, and presentation software package, (LabVIEW 4.0 software, National Instruments Corp.).

Reaction Cartridges

Within a microwave instrument, chemical reactions take place within reaction vessels, known here as cartridges. Cartridges may be of any size or dimension, including those commonly used in chemical laboratories, such as flasks, beakers, vials, and test tubes. Because the invention inherently involves reactions at or near surfaces (i.e., near dielectric surface coatings), preferable cartridges are those with high surface area-to-volume ratios. These types of cartridges include microtiter plates, microarray chips, and "lab-on-a-chip" devices. The latter devices are characterized by small-scale fluidics channels.

Reaction cartridges have discreet locations for one or more microwave reactions to be carried out. The cartridges may be disposable or reusable. The cartridges may contain microwave-susceptible dielectric. Alternatively, if the dielectric is permanently incorporated into the instrument reaction chamber, the cartridges may not have dielectric in their structures.

Chemiluminescent Compounds for Bioanalytical Assays

There are very many chemiluminescent reactions known which efficiently emit light and can be used for bioanalytical purposes. Some classes of CL reactions are (each of which has many structural variations); 1,2-dioxetanes, aryl oxalates, acridinium esters, luminols, and lucigenin. All of these classes have been used analytically, either as labels in immunoassays or as chemiluminescent enzyme substrates. In most cases, the light-emitting chemical reaction that occurs is a bimolecular reaction, often with an oxidizing agent. Hydrogen peroxide and sodium hydroxide are common second reagents. All of the reactions may be accelerated by an increase in temperature. There are vendors of these compounds such that both free CL compounds as well as CL compounds labeled with linkers for protein modification for use in immunoassays.

Before the present invention of microwave chemiluminescence, chemiluminescent compounds were considered either glow or flash type reagents, depending upon whether their reaction rates were slow (glow) or fast (flash) at ambient temperatures. Reaction rates and durations were largely beyond the control of the user. With the current invention, both flash and glow type reagents can also be considered microwave chemiluminescent reagents. Now both types of reactions may be controlled by the user using directed microwave heating. Glow reagents can be caused to flash upon microwaving. Flash reagents can be rendered unreactive by altering the solvent conditions and then induced to flash upon microwaving.

As illustrated in FIG. 3, a diverse variety of chemiluminescent chemistries can be used as microwave chemiluminescent reagents. Typical glow type chemiluminescent reagents are dioxetanes such as compounds 5 and 6 and luminols, such as 1 and 2. Common flash reagents are acridinium esters. Light emission by acridan esters (compounds 3 and 4 in FIG. 3) involves the formation of an acridinium ester intermediate.

Dioxetanes emit light without any secondary reagent such as hydrogen peroxide. In addition, dioxetane CL reactions are remarkably temperature dependent. Dioxetanes are used as glow type regents in enzyme immunoassays and enzyme assays of alkaline phosphatase, glucuronidase, glucosidase, and beta-galactosidase (Tropix, Foster City, Calif.). Dioxetane chemiluminescence is highly temperature dependent, with light emitted rapidly at elevated temperatures. Various dioxetanes are commercially available from Tropix and other sources and methods for conjugating them to proteins have been published. In addition, Tropix sells conjugates, which can be linked to proteins.

Acridinium esters are another class of CL reagents that is useful in MATTR. These compounds react with acids and bases in the presence of an oxidizing agent, resulting in flash type CL. Several acridinium esters are commercially available. Lumigen, Inc. (Southfield, Mich.) sells small, water-soluble chemiluminescent labeling acridinium esters that are triggered by a simple chemical reaction to produce CL as a rapid flash. The chemical kinetics of these compounds can be slowed by judicious dilution of the triggering reagents. A flash of light can then be induced by microwave heating. Another company, Assay Designs, Inc. (Ann Arbor, Mich.), also sells acridinium ester labeling kits. Their acridinium esters link to proteins via NHS ester functional groups. Assay Designs also sells trigger solutions to affect light emission.

MATTR-Based Assays

Figure 6:
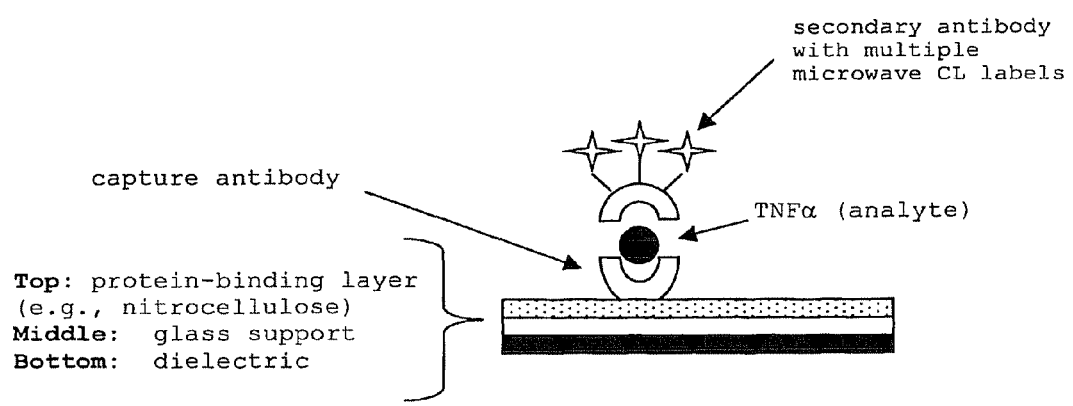
FIG. 6: MATTR-based sandwich immunoassays for TNFα. Upon microwave irradiation, light is emitted from; (A) CL labels indirectly bound to the analyte, TNFα, or (B) from enzyme-generated CL labels.
Figure 6:
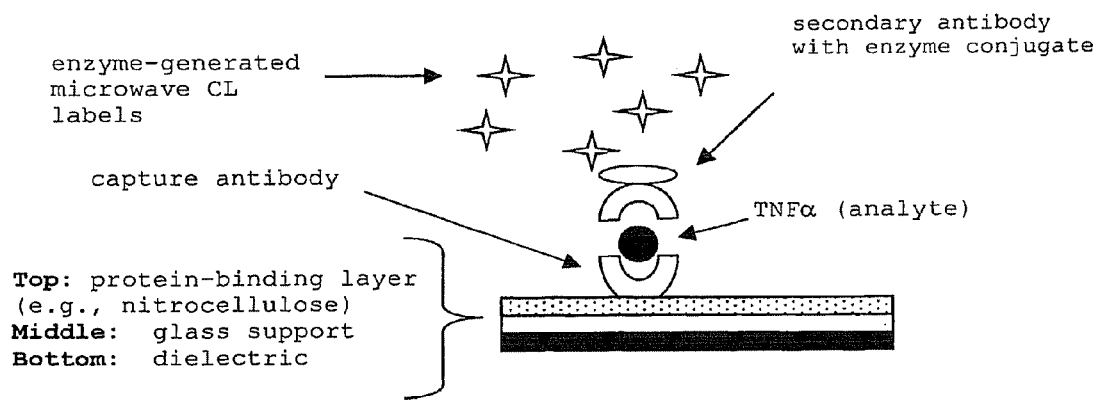

Immunoassays. MATTR-based immunoassays may be conducted in any of a wide variety of formats. For example, a MATTR chip or microtiter plate, with specific capture molecules on it surface, may be exposed to analyte solution, followed by secondary antibody binding (if necessary), and washing (if necessary) (FIG. 6). An alternative to testing analytes in solution is a tissue array, in which immunoassays are performed on thin slices of tissue, usually arrayed on a chip. Tissue array analyses can also be performed using this invention.

Immunoassays are usually performed using either competitive or sandwich immunoassay formats. The signaling label, generally a chemiluminescence or fluorescence generating reporter molecule, will be present on the appropriate surface-bound molecule. Once the binding and washing has been completed, the chip is placed in the MATTR instrument and analysis is carried out.

An example of an immunoassay is one for tumor necrosis factor alpha (TNFα). TNFα is an angiogenic growth factor protein. There are several commercial sources of high quality required reagents, TNFα and appropriate antibody pairs. R&D Systems (Minneapolis, Minn.) sells a CL-based assay for this protein that could be used in a MATTR based assay. The assay is a sandwich enzyme immunoassay. With MATTR, the secondary antibody is labeled with multiple copies of a chemiluminescent compound by means known in the art.

Immunoassays for many different analytes including TNFα have been performed using MATTR technology (see Examples, below).

Figure 1B:
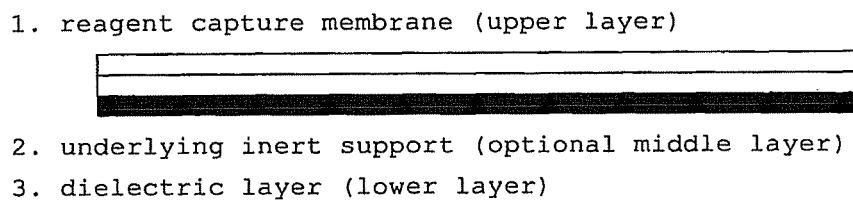
Figure 1C:
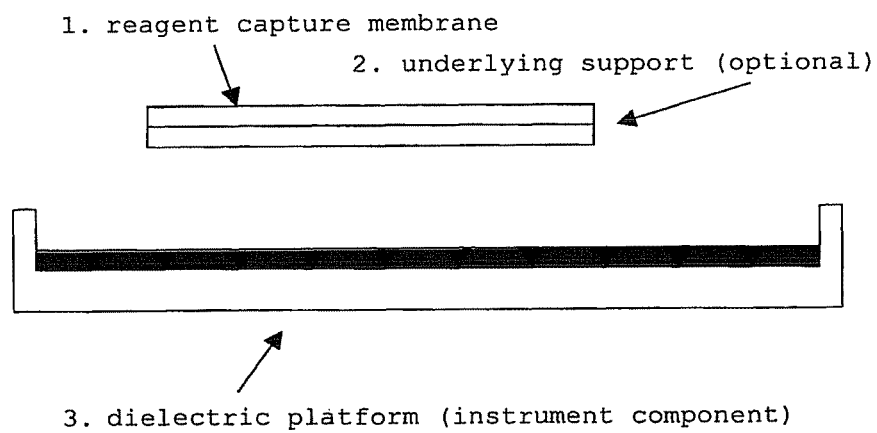

Analysis of Nucleic Acids. MATTR-based nucleic acid analysis will have much in common with immunoassays analysis by the same technology. The major differences are described here. Assays may take place as follows;

(1) A MATTR chip (FIG. 1), with specific capture molecules on its surface, is exposed to analyte solution and the analyte binds to the surface. In one type of assay, the captured analyte is detectable because it itself has been pre-labeled with CL molecules (Schena et al., 1995). The target cDNA can be labeled using any of the many well-known methods and reagents (TriLink BioTechnologies, Inc. San Diego, Calif.; Glen Research Corp., Sterling, Va.). It is preferable to label the target with multiple CL reporter groups. For example, DNA can be chemically biotinylated and the biotin-DNA molecule can bind streptavidin labeled with multiple luminol molecules. Alternatively a sandwich type format can be employed in which a secondary probe is used (Kricka, 1999). In this format, the primary probe, immobilized on the chip, captures the unlabeled target molecule, which in turn captures the CL-labeled secondary probe.

The capture molecule layer is spotted on a nylon membrane. The nylon may be a full-size overcoat or punched into small circles. The actual spotting process is carried out using a manual microarray spotter (Xenopore Corp.), which can deposit spots on a standard 1"×3" microscope slide. The manual microarrayer is a simple bench top device, measuring only 5"×5" and weighing less than three pounds. It requires no external power source. Uncoated or derivatized glass microscope slides, coverslips, porous membranes, gels, or plastics.

(2) Once binding has been completed, the chip is placed in a chip holder in a MATTR instrument and measurement is made. It should be noted that, as expected, the microwave-generated heat will denature the analyte, but the signal will not be affected.

Preparative Applications: Rapid Biomolecular Binding

Almost invariably microtiter plate- or microarray chip-based analyses of protein or nucleic acids require preparation of the plates or chips prior to analysis (Price & Newman, 1997; Wild, 2000) involving coating with a specific protein or nucleic acid. Directed microwave heating can be used to accelerate these preparations by targeting heat to proximal dielectrics, which selectively warm the surface of the plates or chips.

Plate surface-directed microwave heating gives superior results when compared to conventional bulk heating in, for example, a 37° C. incubator chamber. The advantage is related to the fact that in a bulk incubator the entire plate and its contents are uniformly warmed while in surface-targeted microwave heating, the plate binding surfaces are preferentially warmed. Surface binding reactions are therefore preferentially accelerated. Bulk (convection) incubators are currently widely used (Harvard Apparatus, Bellco Glass, Inc., Techne, Inc., Thermo LabSystems, Inc., Boekel Scientific)

There are thousands different types of plate or chip preparative reactions, but typically each involves immobilization of either a binding macromolecule (protein or nucleic acid) or a small molecule ligand. Arrays (libraries) of small molecule ligands such as peptides or other small organic molecules are often synthesized in situ using combinatorial chemistry methods. The technology for macromolecule immobilization and small organic molecule combinatorial chemistry of the present invention is compared to existing technologies below.

It is a distinct advantage of the present invention that surface microwave heating can be used both for preparative reactions and, in the same location, for subsequent analytical reactions. Described below are innovative ways in which preparative and analytical microwave reactions can be used sequentially.

Preparative Applications: Targeted Microwave PCR

Figure 12:
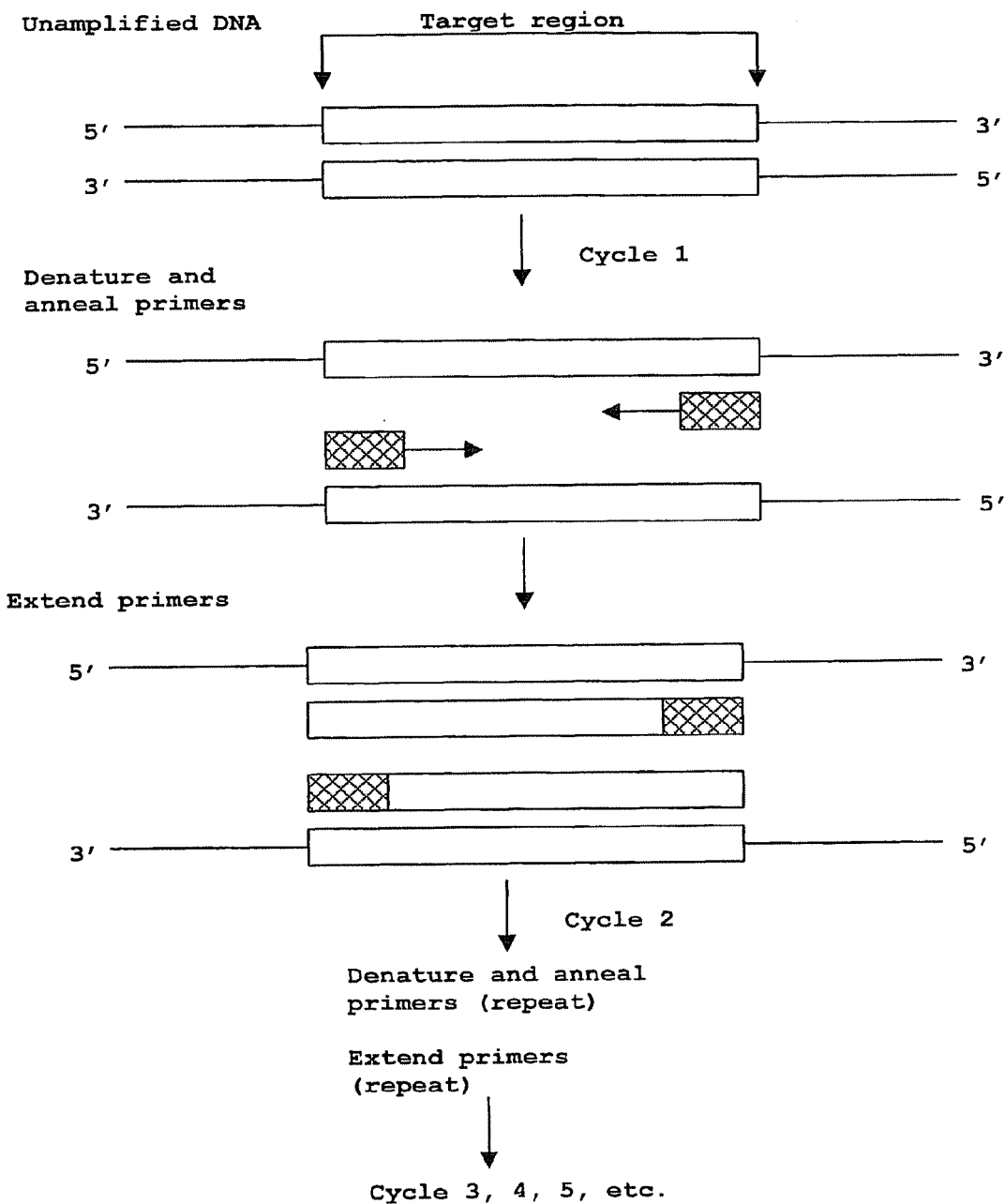
FIG. 12: Polymerase Chain Reaction (PCR).

It is shown here for the first time that directed microwave heating can dramatically accelerate nucleic acid hybridization. Polymerase chain reaction is one practical application where nucleic acid hybridization is essential (McPherson & Moller, 2000; Newton & Graham, 1994). PCR is a nucleic acid amplification method in which a specific nucleic acid sequence is geometrically amplified through an iterative process involving heating and cooling (FIG. 12). In PCR, high temperatures are used to dissociate strands of double-stranded DNA. Using the invention described, two steps—annealing (hybridization) and dissociation—can be accelerated.

Rapid PCR methods are desirable because of their convenience and because of the importance of obtaining test results rapidly in critical lifesaving applications such as biodefense testing (Chen, 2003; Fermer et al, 2003; Gloffke, 2003). PCR hybridization reactions are slower in the earlier cycles of amplification due to the low concentration of template (amplified sample) in comparison to the fairly high concentration of added primer. Conventional PCR is carried out in a temperature cycling instrument called a thermal cycler (thermocycler). Thermal cyclers are widely available bulk heating devices (Constans, 2003). Several designs of thermal cyclers are available based for example on; heating and cooling by fluids, heating by electric resistance and cooling by fluid or refrigerant, heating by electric resistance and cooling by semiconductors (Peltier devices), and heating matt black metal surfaces by light followed by air cooling (Newton & Graham, 1994). Thermal cycler-based PCR is relatively slow—an amplification cycle may commonly take 6 minutes (Example 11).

Of key importance in this invention is that heating is non-contact, but bathed in a microwave. There exist infrared light-heating-based rapid PCR systems (Newton & Graham, 1994; Giardano et al., 2001; Slyadnev et al., 2001). Systems that use light as a heat source have the drawback of requiring a direct line of sight to the PCR reaction. In addition, microwave heating of dielectrics (and subsequent cooling by heat sinks) requires very low power, and is extremely rapid.

The use of microwaves as the heat source in bulk PCR has been demonstrated (Fermer, 2003). In this publication, binding (annealing) reactions were not aided by microwave heating—the reactions were taken out of the microwave during these steps. In accordance with the principles of the present invention, microwaves are employed to accelerate nucleic acid annealing. Moreover, in Fermer et al., the reaction was carried out in bulk solution (0.5 mL plastic tube) without the aid of a proximal solid dielectric—an added advantage of the current invention.

Another temperature-dependent aspect of PCR that is commonly practiced is the sudden introduction of reagents that are entrapped in hollow wax spheres (Newton & Graham, 1994; McPherson & Moller, 2000). The idea is that reagents can be physically isolated by a wax partition until needed. Commercial wax bead products include Taq Bead™ Hot Start Polymerase (enzyme compartmentalization, Promega), StartaSphere™ beads (magnesium compartmentalization, Stratagene). An alternative is to inactivate a reagent with an antibody, which heat denatures. JumpStart™ Taq DNA polymerase (Sigma) is an example of this. The DNA polymerase is temporarily inactivated by a specific antibody, which dissociates upon heating.

In the case of MATTR, the wax or other coating agent can be located in thermal proximity to a microwave-targeted dielectric, and would melt/dissociate to release the desired reagent upon microwaving. The transmission of heat from the dielectric to the coating agent might be especially critical if the coating is made from a microwave-transparent medium, such as paraffin wax (Surrmeijer et al., 1990), that would not heat directly by microwaving.

It is notable that directed microwave release of an entrapped or bound reagent from a heat-dissociable compartment is not restricted to use in PCR. Directed microwave heating can be used as a general reagent delivery system outside of the field of PCR. For example, reagents in an immunoassay could be released by microwaves when needed.

In the embodiment of rapid PCR, MATTR technology can be used to rapidly detect mRNA in cancer cells. Detection of mRNA is useful in determining which of several important cancer-associated proteins are being produced. Analysis will be performed on cDNA prepared from cellular mRNA by RT-PCR. RT-PCR is a powerful and sensitive method for amplifying specific cellular mRNA (Latchman, 1995) and is becoming a powerful method for both qualitative and quantitative molecular diagnostics (Freeman et al., 1999). In RT-PCR, mRNA is isolated (either total or polyadenylated RNA). RNA is then reverse-transcribed to complementary DNA (cDNA) using the retroviral enzyme, reverse transcriptase ("rt"). Primers (gene specific or universal) are required to initiate reverse transcription. Product cDNA is amplified, using PCR or another amplification method, to give detectable quantities of cDNA. RT-PCR is an established method that is often used to detect cancer gene expression (for a review, see Seiden & Sklar, 1996).

Advantages of the Present Invention in Protein and Nucleic Acid Immobilization:

Prior to immunoassays and DNA probe assays, capture molecules are immobilized on microchips or microtiter plates. Immobilization is often accomplished by simple adsorption of the capture molecule to the glass or plastic surface. This procedure usually involves incubation at room temperature for several hours, or at 37° for approximately 2 hours. Elevated temperature heating takes place in a warm chamber (incubator). The present invention discloses two new and improved ways in which molecules can be immobilized. The new ways can be used independently or together. One way is to use microwave heating of the underlying dielectric to gently incubate the surface at approximately 37° C. Another way is to use the piezoelectric properties of underlying ceramic dielectrics to create ultrasonic vibration (sonication), causing the biomolecules to bind to the solid support faster than without sonication. These two methods are described in greater detail below.

(1) Accelerated Immobilization Using Targeted Microwave Heating. Binding of a macromolecule such as a protein or nucleic acid is a surface phenomenon. If the surface is warmed, binding occurs faster. Advantages to microwave surface targeted warming were surprisingly found. By microwaving the binding surface rather than the bulk liquid phase as is normally done, heat is directed to the molecules near the surface. Besides unprecedented capture molecule binding speed, another advantage of using dielectric surface heating is that the same dielectric can be used later for analytical purposes. Protein or DNA capture molecules are bound using microwaves, and then microwaves are used to accelerate a reaction (chemiluminescence, for example) in analyte detection. It has been found that (as is documented in standard protocols) incubating at elevated temperatures such as 37° C. accelerates both non-specific attachment of proteins to surfaces and biospecific (e.g., antibody-antigen) binding on solid phases. Both types of binding can be accelerated by directed microwave surface heating as described herein.

Advantages of the Invention in Solid Phase Combinatorial Chemistry:

Increasingly large libraries of low molecular weight compounds are screened or tested for the ability of proteins or nucleic acids to bind to them. The present invention surprisingly can be used both for synthesis (on chip or plate or other solid support) and for subsequent analysis. First, directed microwave heating is used to accelerated chemical synthesis on the surface, then microwave heating is used in the analysis of the surface (e.g., chemiluminescent receptor binding assay or immunoassay). Advantages of small-scale synthesis, followed by analysis include the fact that less waste is generated (an environmentally-sensitive method) and microwave heating on a small scale uses less energy (microwave heating is in general considered a "green technology").

Solid phase-immobilized libraries of chemical compounds can be synthesized (Dolle, 2000) and screened for activity against biomolecules. For example, peptide libraries can be made to search for lead compounds that bind to a protein receptor. Reports of microwave-assisted combinatorial chemistry have been published (Kappe, 2001; Borman, 2001) and combinatorial chemistry on chips has also been reported (Fodor et al., 1993; Kramer & Schneider-Mergener, 1998; MacBeath et al, 1999). Microwave-assisted combinatorial synthesis on standard (non-dielectric-coated) planar surfaces has been reported (Blackwell, 2003), but not on dielectric-coated surfaces. The advantages associated with dielectric coating are unique to this invention. These include; speedy heating under low microwave power, the ability to direct heat in a pattern on the planar surface, and the ability to use microwaves in post-analysis, for example using directed microwave chemiluminescence.

Smaller libraries (2-1000 distinct chemicals) called focused libraries can be made. The libraries can then be assayed on the same chip using microwave-accelerated reactions to detect binding or catalysis.

Bulk (as opposed to directed) microwave accelerated chemistry has existed in the literature for almost twenty years and is becoming increasingly popular with organic chemists involved in combinatorial chemistry and drug discovery (Lew et al., 2002; Wathey et al. 2002; Kappe, 2002). To fill the growing demand, at least three companies; Personal Chemistry (Uppsala, Sweden), CEM (Wilson, N.C.), and Milestone (Italy) offer instruments and kits for solution phase reactions. All commercial products involve solution phase syntheses in irradiated tubes. Although not yet significantly commercialized, solid phase, solvent-free microwave chemistry is also becoming increasingly visible in the scientific literature (Wathey et al., 2002). Microwave chemistry often reduces reaction times by 10-fold or more, while increasing yields substantially.

On-chip dielectric-directed microwave combinatorial chemistry (MATTR) has not been reported in the before this invention. In MATTR, the reaction mixture is indirectly targeted by microwaves—the dielectric chip is the targeted and heat transfer to the proximal reactants drives the reactions. Evaporation is minimized by an inert chip cover, if necessary. In essence, MATTR for the first time unites the fields of microarrays, combinatorial chemistry, and microwave chemistry. On-chip libraries can be prepared using spots on a contiguous chip surface (e.g., nitrocellulose membrane) or by using surface membrane-entrapped beads. Functionalized beads are commonly used in conventional combinatorial chemistry.

Until now, on-chip synthesis has been unattractive because in many cases the size of the effort was not worth the information gained in an experiment. Conventional (long) reaction times were necessary to prepare chips that would be used only once or twice, and then discarded. MATTR will drastically reduce the synthesis time so that synthesis and analysis can be done in a single day. Moreover, MATTR is a low-solvent volume chemistry that generates little waste.

Directed chemistry is described above as the small-scale synthesis of chemical libraries on, for example chips or plates, followed by bioanalysis for binding to a molecule such as a protein. However, there is no reason to preclude the use of directed microwave synthesis in larger scale synthesis. Larger quantities, milligrams or grams, of a compound could be synthesized as well. Thus, attractive medicinal qualities of a molecule could be discovered by on-chip synthesis and detection, and rapid directed microwave synthesis could then be used to scale up production for further detailed studies.

Use of MATTR To Decontaminate Samples After Analysis.

MATTR-based analyses could often involves testing of toxic or pathogenic specimens. For example, in the field of biodefense, tests for toxins such as the protein ricin, or pathogens such as the bacterium anthrax could be carried out. These samples would need to be decontaminated after analysis. Using MATTR, samples could be decontaminated using microwave heating. In decontamination, a MATTR chip, plate, or other disposable cartridge would be heated to inactivate or denature the pathogen or toxin. For example, a bacterium could be inactivated by heating in excess of 160° C. for 5 minutes. A proteinaceous or nucleic acid toxin could similarly be denatured. Thus, a MATTR-based analysis can encompass one or more aspects of microwave-accelerated preparation, analysis, and decontamination.

Having now generally described the invention, the same will be more readily understood through reference to the following Example, which is provided by way of illustration, and not intended to be limiting of the present invention.

Example 1

Microwave Detection of Luminol and Isoluminol

Luminol (3-aminophthalhydrazine) and isoluminol (4-aminophthalhydrazine) (FIG. 3, compounds 1 and 2, respectively) are two chemiluminescent compounds that are commonly used in bioanalyses. Normally, they are made to emit light; through the action of an enzyme such as horseradish peroxidase (HRP), in a non-enzymatic ambient temperature chemical reaction, or through an electrochemical reaction. (Iso)luminol have not been reported to emit light upon directed microwave heating. It is not obvious that rapid microwave heating would cause (iso)luminol to emit light—rapid heating could destabilize the molecules, resulting in a breakdown by non-light-producing pathway(s). Moreover, in accordance with the principles of preferred embodiments of the invention, conditions are sought in which little or no chemiluminescent reaction occurs at room temperature, but an extremely fast reaction (approaching a "flash") occurs under mild microwave heating.

Luminol and isoluminol rapidly react with oxidants at alkaline pH to produce light at room temperature. Numerous conditions are tested at room temperature and under microwave heating. Variations included buffer (sodium bicarbonate, sodium phosphate, Taps, imidazole, Hepes, Bes), pH (6.5, 7.5, 8.39, 8.55, 8.71, 9.10), oxidants (hydrogen peroxide, sodium perborate, potassium permanganate, iodine), and enhancers (copper sulfate, 4-iodophenol, cobalt chloride).

Room temperature reaction rates were measured at various concentrations of reactants in 96-well plates. Plates were read in a luminometer (Thermo Labsystems Ascent).

Microwave heating reaction rates were tested on FAST Slides (S&S Biosciences, Keene, N.H.), which are nitrocellulose-coated microscope slides, and on HydroGel Slides (PerkinElmer), which are hydrogel-coated microscope slides. Both types of slides were undercoated with microwave-active dielectric material (BSR-1 SS6M, 0.01", Emerson & Cuming, Randolph, Mass.). Luminol (Alfa Aesar, Ward Hill, Mass. and Alpha Innotech, San Leandro, Calif.) and isoluminol (Sigma, St. Louis, Mo.) were spotted on the slides using a hand microarrayer (S&S MicroCaster), which deposited 3-5 nL spots. Combined remaining reagents were sprayed to uniformly wet the slide. The slides were placed in a clear plastic protective holder and X-ray film (ECL Hyperfilm, Amersham) was placed against the holder facing the reactants. Light was recorded on the film either at room temperature or during microwave heating (for generally 30 sec) in a GE microwave oven (600 W, Model JE635WW 06).

Throughout the experiment, light emission yield from luminol (was consistently higher than from isoluminol. Isoluminol and luminol responded similarly to changes in reaction conditions, indicating that the chemical mechanisms of the two compounds were essentially the same. The spray reagent found to be most suitable for directed microwave detection of luminol and isoluminol included; 67.5 (or 125 mM) mM $NaBO_3$, 100 mM $NaHCO_3$ (pH 7.6), and 0.0175 g/L $CoCl_2$. These conditions gave a very slow room temperature chemiluminescence reaction, but a very fast reaction under mild microwave heating (approx. 100° C.). The reaction rate ratio (microwave/room temp.) was estimated to be greater than 1000.

The detection limit for both FAST- and HydroGel-based dielectric slides was 853 amol of luminol. Isoluminol showed a detection limit 8-10 times lower than luminol.

Example 2

Microwave Detection in an Immunoassay Using Isoluminol-Labeled Antibody

Example 1 showed that small amounts of (iso)luminol (2, FIG. 3) could be detected using microwave directed chemiluminescence. An experiment was carried out to see if microwave directed chemiluminescence could be used to detect an analyte in an immunoassay. Another purpose of the experiment was to see if a direct-labeled (isoluminol) antibody could be used.

In the experiment, mouse IgG (Sigma I-5381) was used as the analyte. Mouse IgG (1 mg/mL) was spotted (3-5 nL) on a chip (FAST Slide) in S&S Array Buffer. Analyte was detected using streptavidin-isoluminol (3.5 labels per streptavidin, Sigma S-8532) that was bound to the recognition antibody, which was a biotin goat anti-mouse antibody (Sigma B-7151). Chemiluminescence of chips (BSR-1 dielectric undercoated FAST Slides) was measured on X-ray film following spraying with reagent (see Example 1) at room temperature or upon microwaving.

Detection was performed on BSR-1/SS6M or MCS/SS6M dielectric (Emerson & Cuming) undercoated slides—either FAST Slides (S&S) or homemade nitrocellulose coated microscope slides. Homemade slides are made by spraying microscope slides with Elmer's spray adhesive and placing Protran nitrocellulose (S&S) on the sticky slide.

Initially, streptavidin-isoluminol was spotted and detected at various concentrations and found to have a microwave-directed chemiluminescence detection limit of approximately 22.7 fmol of streptavidin.

For detection of mouse IgG, the following protocol was followed. Analyte spotted chips were blocked with S&S Wash/Block buffer for 2 hours at room temperature on a rocker. Chips were then washed 3 times for 5-10 minutes with the same buffer. The pre-formed complex of (biotinylated goat anti-mouse antibody)[streptavidin-isoluminol] was then added and the chip was incubated at room temperature on a rocker for 5 hours. The chip was then washed as described above.

The chips were sprayed with the reagent described in Example 1, and microwaved for 30 seconds. Microwave chemiluminescence light emission was captured on X-ray film. Spots corresponding to the analyte spots were visible on the scanned film, indicating that; (1) microwave chemiluminescence immunoassays can be performed, and (2) sensitive detection of a direct label (unamplified signal) is possible.

Example 3

Microwave Detection of Chemiluminescent Enzyme Substrates

Having discovered that (iso)luminol can be used in microwave chemiluminescence analyses, experiments were conducted to determine if other chemiluminescent chemistries were also amenable to microwave triggering. Chemiluminescent compounds can often be used as direct labels (attached to proteins or nucleic acids) or enzyme substrates. Streptavidin-isoluminol is an example of the former and luminol (an HRP substrate) is an example of the latter. Enzyme substrate chemiluminescent compounds have the advantage of catalytic amplification, but they also have the drawback of light emission being a sustained low glow. Chemiluminescent enzyme substrates usually follow the pathway shown below;

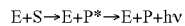

where E is enzyme, S is substrate, P* is a transient product, P is final product, and hv is light emission. Metastable product P* spontaneously breaks down to form P and light. Thus, if enzyme catalysis is slower than the conversion of P* to P, then a glow directly corresponds to the time course of enzyme catalysis. If enzyme turnover is faster than the conversion of P* to P, then P* accumulates and slowly breaks down in a glow. In either case, glow chemiluminescence can be very time consuming (hours) and often results in interfering background signal, which builds up with time. The goal was to convert the conventional pathway (above) into one where little or no glow occurs, but instead a microwave-induced flash;

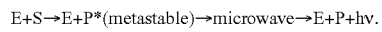

Numerous chemiluminescent enzyme substrates with diverse chemistries are commercially available. The goal was to test a representative range of substrates and develop as many as possible as microwave substrates. The compounds tested were; APS-5 (3 in FIG. 3, Lumigen, Inc., Southfield, Mich.), PS-3 (4 in FIG. 3, Lumigen), Lumi-Phos Plus (LPP, 5 in FIG. 3, Lumigen), and CDP-Star with Nitroblock II (6 in FIG. 3, Tropix/Applied Biosystems, Bedford, Mass.). Of these, APS-5, LPP, and CDP-Star are sold as alkaline phosphatase (AP) substrates, and PS-3 is sold as a horseradish peroxidase (HRP) substrate.

Although these are enzyme substrates, they were first tested them with microwave heating in the absence of enzymes to determine whether they might have chemistries that cause them to emit light under directed heating.

1.0-2.0 μL of substrates (APS-5, PS-3, LPP, CDP-Star, all supplied as liquids) were therefore spotted on dielectric chips (BSR-1/SS6M undercoated, Protran nitrocellulose coated microscope slides), and read light emission (30 or 60 seconds, room temperature or microwave) on X-ray film (Amersham Hyperfilm ECL). One of the compounds, APS-5, was detected at room temperature, and the light emission intensity became substantially greater when microwaved.

The experiment was then repeated the experiment, but the chips were sprayed with oxidant solution before detecting light emission (see Example 1 for spray reagent). Here, both APS-5 and PS-3 emitted light at room temperature and much more light under microwave heating. Light emission from APS-5 appeared greater than the light emission in the absence of oxidant.

The goal was to modify the reagent spray in order to lower the room temperature reactions, but not the microwave reactions, of APS-5 and PS-3. Various solutions including sodium bicarbonate (0.2 M, pH 9.6 and 7.5) and oxidant spray with cobalt concentration varied were tried without success. It was found that using the spray oxidant listed in Example 1, but replacing sodium bicarbonate with equimolar amount of Tris buffer, pH 9.3 gave a very good result for APS-5. The microwave/room temperature light emission ratio was estimated to be 100 and the APS-5 detection limit was approx. 1 fmol.

The goal was to identify conditions whereby PS-3 would emit little light at room temperature but much light under mild microwave heating. the effect of the compositions of the Tris, pH 9.3 reactant spray described above were explored by varying pH (10.1, 11.1, 12.0), varying the concentration of $NaBO_3$, and comparing $NaBO_3$ to $H_2O_2$ as the oxidant. It was found that the best conditions for PS-3 were the same as for APS-5 (Tris solution), but with a pH of 11.1.

In conclusion, APS-5 and PS-3, but not LPP or CDP-Star, were found to emit light in the absence of enzyme. In both cases, chemical triggers gave substantially more light under microwave heating.

Example 4

Enzyme-Amplified Microwave Detection of Chemiluminescent Compounds

The results of Example 3 showed that APS-5 and PS-3 chemiluminescence can be detected in the absence of enzymes and that the intensity of this non-enzymatic chemiluminescence is greatly enhanced by directed microwave heating. Next, experiments were conducted to determine if enzyme-catalyzed luminol, APS-5, LPP, PS-3 and CDP-Star could be adapted to directed microwave-enhanced detection. Because these substrates are designed to emit light upon enzymatic catalysis, it was important to find conditions whereby enzyme catalysis (S→P* in Example 3) and light emission (P*→P+hv) could be decoupled—in other words, conditions in which catalytic conversion of substrate to metastable product is rapid, but subsequent conversion to final product (P) and light was minimal. The second step (P*→P+hv) would then be triggered by directed microwave heating. If this were possible, then microwaves would trigger a sudden burst of light from the accumulated metastable product.

luminol and PS-3 were investigated with the enzyme horseradish peroxidase (HRP) and APS-5, CDP-Star, and LPP with the enzymes acid phosphatase (AcP) and alkaline phosphatase (AP). In this Example, it is shown that for all five enzyme substrates listed above, reaction conditions were found under which light output at room temperature was minimized and rapidly restored by microwave heating.

Experiment 1: Horseradish Peroxidase (from horseradish, Sigma P-8125) with luminol and PS-3. Each substrate was looked at individually.

HRP and luminol. In the absence of enzyme, luminol reacts at alkaline pH with oxidants such as $H_2O_2$ and $NaBO_3$.

This reaction is accelerated by HRP. The natural pH optimum of HRP catalysis is around 6.0-6.5, but the optimum pH of luminol light emission is at pH 9 or greater. It was anticipated that by running the HRP-luminol reaction at near neutral pH, the enzyme reaction would proceed at a rapid rate, but the subsequent light emitting reaction would be slow or inert, until triggered by microwave heating.

0.5 µL each of luminol+/−HRP (50 ng)+/−$H_2O_2$ (10 mM) were spotted on Protran nitrocellulose-coated, BSR-1/SS6M dielectric-undercoated slides. Some of the slides were sprayed with the spray reagent described in Example 1 except that the buffer and pH were modified. Three minutes after spraying, the light emission at room temperature or under microwave irradiation for 10, 30, or 60 seconds was measured. X-ray film (ECL Hyperfilm) was used to detect and measure light emission. The buffers tested were Tris at pH 6.6, 7.0, 7.1, 7.2, 7.7, and 9.3. The results showed a pH dependence of light emission—the trend showed more light was given off at higher pH values. Substantial light was given off at room temperature. Microwave heating enhanced light emission, but only by 2-fold or less. These data suggest that enzyme catalysis and light emission are strongly coupled in the luminol/HRP reaction.

HRP and PS-3. It was found that one could decouple HRP catalysis and light emission in this reaction. Under these conditions, HRP catalyzed PS-3, but very little light was emitted until the dielectric chip was microwaved.

HRP, PS-3, and $H_2O_2$ (0.5 µL each) was spotted on Protran nitrocellulose, BSR-1 dielectric chips, incubated at room temperature for 3 minutes, then read at room temperature or under microwave heating for 30 seconds. HRP was diluted into various buffers including pH 9.3 (50 mM Tris), pH 6.5 (50 mM BES), pH 7.5 (50 mM HEPES). The results with HEPES, pH 7.5 buffer were spectacular—little or no light emission occurred at room temperature, but upon microwaving very dark spots were seen on the X-ray film. No spots were seen if HRP was left out. This indicates that a metastable intermediate (P* above) accumulates and that the intermediate breaks down under microwave heating, but not at room temperature.

Experiments were also conducted with HRP, PS-3, and $NaBO_3$ (sodium perborate tetrahydrate, Aldrich 244120), in the complete absence of $H_2O_2$. Perborate buffers gave better light output when used as an oxidant in place of peroxide. The best substrate/buffer solutions for microwave-enhanced chemiluminescence were found to include 5-25 mM perborate, 100 mM PIPES buffer, pH 7.0, and 50% (v/v) PS-3 substrate. These buffers gave high enzyme activity, low light output at room temperature, and high light output under microwave heating.

Experiments were also conducted to investigate the use of perborate-containing buffers in the HRP/PS-3 detection system. These included pH studies and inclusion of cobalt ion. Ultimately, it was found that the best substrate/buffer for the HRP/PS-3 microwave detection system was 50% (v/v) PS-3 (Lumigen), 40% phosphate-citrate (50 mM) buffer with sodium perborate (0.03%), pH 5.0 (Sigma P-4922), and 10% (v/v) 250 mM sodium perborate. The use of 10% (v/v) 125 mM perborate instead of 250 mM gave similarly successful results.

Experiment 2: Alkaline Phosphatase (bovine intestinal mucosa, Sigma P-6774) with CDP-Star, LPP, and APS-5. Each substrate was looked at individually.

CDP-Star (Applied Biosystems, supplied as 0.25 mM "ready-to-use" with Nitroblock II) was mixed with nothing ("straight"), or mixed 1:1 with water (control), Tris (pH 8.0, 250 mM), glycine (pH 9.0, 250 mM, or $NaHCO_3$ (pH 10.0, 250 mM). Substrate was mixed 3:1 with enzyme (approx. 1 u/µL) and the mixtures were spotted (0.2 µL) on a Protran-coated, BSR-1/SS6M dielectric undercoated slide. X-ray film measurements at times between 0 and 30 minutes of incubation (room temperature and microwave readings) showed a dramatic effect of microwave heating, especially with Tris buffer, and less with bicarbonate buffer. Room temperature readings were faint while microwave readings were dark.

Lumi-Phos Plus (LPP, Lumigen, Inc. supplied ready to use) was tested as described above for CDP-Star. LPP gave similar results to CDP-Star—there was little light emission at room temperature, but dramatic light emission under brief microwave irradiation. The darkest spots on film were from straight LPP (undiluted). The other spots all gave substantial emission and there was no strong pH or buffer effect.

APS-5 (Lumigen, supplied ready to use) also showed microwave-enhanced light emission when tested in the same manner as CDP-Star and LPP. However, this substrate shows quite a bit more background emission than the other substrates. Non-enzymatic room temperature light emission (see above) was observed, as well as much more enzyme-catalyzed light emission without microwave triggering.

In conclusion, all three alkaline phosphatase substrates tested showed microwave-enhanced luminescence. CDP-Star and LPP showed little background luminescence in the presence of enzyme until microwaved, indicating that metastable intermediate (P* in Example 3) was accumulating. APS-5 showed relatively high non-enzymatic and enzymatic room temperature emission suggesting that P* was much less stable than it is in CDP-Star and LPP.

Experiment 3: Acid Phosphatase and CDP-Star, LPP, and APS-5. Acid Phosphatase (Type IV-S from potato, Sigma P-1149) was tested as an enzyme signal amplifier. This enzyme is optimally active at pH 5-7. If signaling reactions are run at the optimum pH of this enzyme, the enzyme-catalyzed portion of the reaction would be fast (S→P*), but the optimally-alkaline light emission step might be slow (P*→P+light), until induced by sudden microwave heating.

The experiment was carried out as described above for alkaline phosphatase, except buffers used were; sodium acetate (pH 5.0, 250 mM), imidazole (pH 6.0, 250 mM), and sodium phosphate (pH 7.0, 250 mM). Enzyme/substrate incubations were varied from 0-30 minutes on chips prior to X-ray film reading at room temperature or under microwave heating.

The results showed that CDP-Star is a substrate of acid phosphatase at pH 5.0. Spots could only be seen on film when the chips were microwaved, but not at room temperature. CDP-Star appears to be a much better substrate of alkaline phosphatase than acid phosphatase. No enzyme activity could be detected with either LPP or APS-5 under any conditions tested.

Example 5

Microwave Detection of Chemiluminescent Compounds on Chips

In accordance with the principles of preferred embodiments of the present invention, molecules on chips can be detected by microwaving the chip and detecting emitted light using X-ray film facing the chip. Alternatives to this method were discovered during this work.

In one alternative, the invention provides a method in which the chip on which the molecules would retain function following microwave analysis. In most cases, the chips had been used once, and then discarded. The heat (generally 90-100° C.) is believed to denature the biological reagents (antibodies, etc.) on the chip. A "blot" method, in which the substrate is not directly applied to the original chip, but instead wetted a glass slide covered with a layer of nitrocellulose and undercoated with BSR-1/SS6M dielectric was investigated. This second chip was pressed against the original chip for a period of time corresponding to the assay time (usually 2-3 minutes). The second chip was then removed from the original chip and assayed for enzymatic product. Assays were performed either by room temperature or microwave chemiluminescence.

Various membranes were successfully used including; AE-100 nitrocellulose (Schleicher & Schuell), Unisart CN200 nitrocellulose (Sartorius), GFF Conjugate pad (glass fiber, Millipore), SNHF 04000 slow flow lateral membrane (Millipore), and Protran nitrocellulose (Schleicher & Schuell). The use of Immobilon P PVDF (Millipore) was investigated, but this membrane was found to wet poorly. To generate light, HRP, PS-3, and $H_2O_2$ was spotted on the original chip, blotted, and then the second chip was read. Results showed that dark well-defined light emission spots were seen on the secondary chip, indicating that the product of PS-3 remained on the second membrane after catalysis. This experiment demonstrated that spots on the original chip could be non-invasively assayed by directed microwave heating.

A variation of the above experiment was performed. In this "overlay" method, the second chip had no dielectric undercoating. When wetted with substrate, the second chip was overlaid onto the original chip. It was found that when the membrane was wet, the second chip (and the glass slide backing) were essentially transparent to light. Thus, the second chip could be overlaid on the original chip and light could be detected through the back of the second chip. This format is attractive, because the second chip provides protection from the film (or camera or PMT). Experiments showed that the "overlay" method gave sharply defined dark spots on film corresponding to enzyme-catalyzed, microwave-triggered chemiluminescence.

Example 6

Microwave Chemiluminescence Detection in an Immunoassay

Chip-based immunoassays were performed to see if enzyme-amplified microwave-enhanced chemiluminescence could be used as a detection method.

Experiment 1: An assay for mouse IgG protein (the analyte) was carried out as follows. BSR-1/SS6M undercoated FAST slides (nitrocellulose, Schleicher & Schuell) were used as chips. Mouse IgG (Sigma I-5381, reagent grade) was dissolved to 0.5 mg/mL in Schleicher & Schuell Array Buffer and spotted on chips, either by pipetting (0.2 µL) or by spotting with a microarrayer (S&S MicroCaster). After arraying, the chips were covered with S&S hybridization chambers and blocked with S&S Wash/Block Buffer for 2 hours on a rocker. The buffer was replaced with biotinylated goat anti-mouse antibody (Sigma B-7151, Fab specific) at concentrations of either 0.5 µg/mL or 100 ng/mL, again in S&S Wash/Block Buffer. The chips were allowed to incubate for 90 minutes on a rocker then washed twice with S&S Wash/Block Buffer, then washed twice with PIPES buffer (83 mM, pH 7.00). The detection enzyme, streptavidin-horseradish peroxidase (SA-HRP, Amersham RPN1231 diluted 35,000:1), was then bound to the biotinylated complex as recommended for 45 minutes. The chips were washed with S&S Wash/Block buffer (2×10 min.) and PIPES buffer (3×10 min.).

Chips were overlaid with a layer of S&S AE100 nitrocellulose membrane (which becomes transparent when wet) and wetted with oxidizing buffer (1:1 mix of PS-3 substrate (Lumigen) and 25.0 mM $NaBO_3$, 100 mM PIPES, pH 7.0). Chips were incubated for 2-minutes at room temperature. Subsequently, light emission was read for 30 seconds, either at room temperature or under microwave irradiation (600 W). Light emission was read on Hyperfilm ECL (Amersham) film.

Results showed that one could see very dark spots corresponding to analyte on chips. Spots were very dark, so the oxidant concentration was lowered to 0.5 and 5.0 mM $NaBO_3$, with 5.0 mM giving better results. Although one could see spots in control experiments (room temperature), the spots were significantly darker under microwave, irradiation.

Experiment 2: An immunoassay for mouse IgG was performed on HydroGel™ Slides (PerkinElmer). HydroGel slides are glass slides coated with a thin layer of clear hydrogel for protein analysis. Slides were prepared and used essentially according to the vendor's instructions. Mouse IgG (the analyte, Sigma Chem. Co., Cat. # I-5381) was spotted at 0.5 mg/mL using a MicroCaster Arrayer (S&S), which gives spots of 3-5 nL volume. Chips were blocked using S&S Wash/Block Buffer then incubated with goat anti-mouse IgG antibody (biotinylated FAB-specific, Sigma B-7151) at concentrations ranging from 0.01-1.0 µg/mL in the same buffer. After washing, the chips were incubated with Amersham Streptavidin-HRP (Cat. RPN 1231), then washed again. Chips were undercoated with BSR-1 dielectric for reading. Chemiluminescent reagent was the same as described above in Experiment 1. Chips were read generally with a 2 minute room temperature incubation to allow enzyme catalysis, followed by equal-time room temperature or microwave analysis on X-ray film. Microwaving (600 W, 2450 Hz) was generally for 30 seconds. The results showed faint light emission at room temperature analysis but very dark spots under microwave analysis. These results show that microwave chemiluminescence is superior to stand chemiluminescence on HydroGel™ chips.

Example 7

Microwave Chemiluminescence Detection of Cytokines and IgG

Numerous experiments were performed to see if microwave chemiluminescence could be used to detect a diverse range of analytes in several immunoassay formats. The analytes included the human cytokines tumor necrosis factor alpha (TNF-α), interferon gamma (IFN-γ), and interleukin 1 beta (IL-1β). The formats included chips that had assay surfaces that were coated with hydrogel (PerkinElmer), nitrocellulose membranes (Panomics, Inc.), and nitrocellulose casts (S&S). In different experiments, capture antibodies were variously arrayed by hand spotting (using a pipettor or hand microarrayer), mass commercial spotting, and custom-commercial spotting.

Experiment 1. Schleicher & Schuell Provision Slides contain a pre-spotted array of 16 different anti-cytokine capture antibodies spotted on cast nitrocellulose. This commercially available chip is used to monitor and measure human cytokines. It is sold in kit form with reagents for immunoassay steps and also comes with instructions for conducting an on-chip immunoassay for a panel of cytokines.

Two cytokines were measured, separately and together—IFNγ (human recombinant, R&D Systems Cat#285-IF) and TNFα (human recombinant, R&D Systems Part#840121). The analytes were measured at a range of concentrations, 128 fg/mL-1 ng/mL TNFα and 192 fg/mL-3 ng/mL IFNγ. The assay matrix was S&S Wash/Block Buffer. The Provision manufacturer's instructions were essentially followed using the kit components to form sandwich immunoassay complexes on the chips.

For detection, chips were undercoated with Emerson & Cuming BSR-1 dielectric. Detection reagent, consisting of 50% PS-3 (Lumigen), 40% citrate/phosphate/perborate (Sigma), and 10% 250 mM sodium perborate, was applied to the chip and dabbed to remove excess liquid. Following a 2-minute room temperature incubation to allow enzyme catalysis, the chip was microwaved (600 W, 2450 MHz) for 30 seconds. Light was captured on X-ray film for a total of 60 seconds (during 30 seconds of microwaving plus an immediate additional 30 seconds).

Scanned X-ray films showed that the cytokines could be detected down to 1.6 pg/ml TNFα (possibly 68 fg/mL was borderline-visible) and 2.4 pg/mL IFN-γ (96 fg/mL was borderline-visible). In a control chip with no dielectric backing, not even the highest TNFα concentration of 1 ng/mL could be detected. This experiment was shown to be reproducible.

Experiment 2: TNFα detection on nitrocellulose-coated FAST Slides (S&S) was performed using microwave chemiluminescence detection. The manufacturer makes FAST Slides using a casting process to coat glass slides with porous nitrocellulose.

Human TNFα and antibodies for detection were obtained from R&D Systems (DuoSet ELISA Development System, Cat. # DY210). The kit contained capture antibody, detection antibody, TNFα standard, and streptavidin-HRP. Standard protocols were used for washing and incubation. Capture antibody was spotted on slides using a hand pipette. Incubations were carried out with rocking using chip hybridization chambers (S&S). Analyte (TNFα) was used at 2.0 ng/mL.

Assays were performed on six chips. Chips were analyzed at room temperature with no microwaves and by microwave chemiluminescence (essentially as in Experiment 1 above). Chips were undercoated with BSR-1 dielectric. The results on X-ray film showed that microwave chemiluminescence resulted in dark spots on the X-ray films corresponding to the chip locations of TNFα capture antibody but no spots could be seen in the standard chemiluminescence analysis, either by eye or following digital scanning. These data show that microwave chemiluminescence gives much greater signal than corresponding conventional chemiluminescence on FAST Slides.

Experiment 3: Microwave Chemiluminescence detection on Panomics membrane arrays was also tested (TranSignal™ Human Cytokine Antibody Array 1.0). Panomics nitrocellulose membranes are unsupported nitrocellulose pre-spotted with antibodies for an array of cytokines. Capture antibodies for 18 cytokines are spotted in duplicate. The membranes also have positive and negative control spots. Human TNFα (2.0 ng/mL, R&D Systems) was used as the analyte. The immunoassay protocol was followed according to instructions, except for the detection. Panomics recommends conventional chemiluminescent detection of cytokines on membranes. Two membranes were assayed and detected using the chemiluminescent reagent described above in Experiment 1. The membranes were placed on BSR-1 undercoated microscope slides for analysis. The membranes were measured at room temperature after a 1-5 minute incubation to allow enzyme catalysis and under microwave conditions (600 W, 2450 Hz, 30-45 sec.). Spots on non-microwave membranes were barely visible on X-ray film, but microwave chemiluminescence spots were sharp and dark. The positive controls and TNFα spots were very dark, but no signal was seen from any of the other cytokine spots. This demonstrates that microwave chemiluminescence is superior to standard chemiluminescence using Panomics membrane antibody arrays.

Experiment 4: An immunoassay for the cytokines TNFα and IL-1β was performed using FAST™ Slides that were custom spotted by Schleicher & Schuell. Slides were purchased that were pre-spotted with 1 mg/mL TNFα and IL-1β capture antibodies, each in a 3×3 array (18 spots total). Equimolar cytokine mixtures were assayed on five chips. Each chip was used to detect a different cytokine concentration; 0.05 ng/mL, 0.1 ng/mL, 0.5 ng/mL, 1.0 ng/mL, and 5.0 ng/mL. Analyte solutions of human TNFα (R&D Systems, Cat#210-TA) and human IL-1β (R&D Systems, Cat#201-LB) were made up in S&S Wash/Block Buffer. Chips were each enclosed in a hybridization chamber and blocking, washing, and binding steps were carried out essentially as recommended by S&S for FAST Slides using S&S Wash/Block Buffer. Biotinylated secondary antibodies and streptavidin-HRP were from R&D Systems (anti-TNFα was from DuoSet kit, and anti-IL-1β was Cat# BAF201, and streptavidin-HRP (diluted 200:1) was Part 890803). Chips were undercoated with BSR-1 dielectric for reading. Chemiluminescent reagent was the same as described above in Experiment 1. Chips were read generally with a 2 minute room temperature incubation to allow enzyme catalysis, followed by equal-time room temperature or microwave analysis on X-ray film. Microwaving (600 W, 2450 Hz) was for 15-30 seconds. The results showed that the lowest concentration of tested cytokines (0.05 ng/mL) could be detected with microwave chemiluminescence and individual points could be resolved, even though they were closely spaced (1.6 mm between spots). Both cytokines were visible with IL-1β giving a slightly greater emission. These results show that microwave chemiluminescence is superior to stand chemiluminescence on custom pre-spotted chips, that both IL-1 and TNFα could be detected at 0.05 ng/mL, and that micrometer spot-to-spot resolution is possible.

Example 8

Microwave-Accelerated Antibody-Antigen Binding

The invention demonstrates surface-targeted mild microwave heating causes acceleration in the rate of biospecific protein binding. This is described here for binding of goat antibody binding to mouse IgG (the antigen), and for mouse antibodies binding to human TNFα and IL-1β.

In the first case (biotinylated goat antibody binding to mouse IgG), approximately 4 nL of 0.5 mg/ml mouse IgG in PBS was spotted on FAST slides (S&S) and allowed to air, dry for 3 hours. The slides (or "chips") had been undercoated with adhesive-backed BSR-1 dielectric (0.01 inch thick, Emerson & Cuming, Randolph, Mass.). The chips were washed 3 times with S&S Wash/Block buffer (S&S, Keene, N.H.), and then blocked for 1 hour in the same. One set (4) chips was subjected to mild microwave incubation with goat anti-mouse antibody (1 µg/ml) while the other set (4) of chips was subjected to room temperature incubation (same concentration of antibody). Room temperature incubation (24-27° C.) was for 60 or 120 minutes. Microwave incubation was for 10 minutes, in the range of 30-49° C. Following incubation, the chips were again washed in S&S Wash/Block buffer. The chips were then incubated for 45 minutes in streptavidin-HRP (Amersham) that had been diluted 500:1 in PBS. The chips were then washed in S&S Wash/block buffer.

The chips were read using microwave chemiluminescence. The substrate mixture included five parts Lumigen P-3 substrate, four parts Sigma citrate/phosphate/perborate buffer, pH 5.0 (Cat #P-4922), and 1 part 250 mM sodium perborate (Aldrich Cat. #244120). The chips were incubated for 2.0 minutes to allow for enzyme catalysis, and then microwaved for 30 seconds. Emitted light was read on Hyperfilm (Amersham) autoradiography film. Only one of the four room temperature incubated showed binding of antibody to antigen. However, the chips that had been mildly microwaved for 10 minutes showed bold spots where antibody bound to analyte. These results showed that directed mild microwave heating is far superior to room temperature incubation in allowing antibody to bind to antigen.

In the second case, it was found that specific mouse antibodies bind much more rapidly to the cytokines TNFα and IL-1β when mildly microwaved than when incubated conventionally at room temperature. In these experiments, "sandwich" immunoassays on FAST slides (S&S) that had been pre-spotted with a capture antibodies specific for each of the two cytokines (S&S Biosciences, Keene, N.H.). Adhesive undercoats of BSR-1 dielectric (Emerson & Cuming) were applied. Immunoassays were performed using cytokines and secondary antibodies from R&D Systems (Minneapolis Minn.). Three types of immunoassays were performed: (1) standard room temperature assay (2-hour capture antibody-antigen incubation and 2-hour secondary antibody-antigen incubation), (2) short room temperature assay (as above except using two 10 minute incubations), and (3) short microwave assay (same as above except both incubations were 10 minutes under mild microwaving). These three types of assays were performed in triplicate (three chips each). The chips were then blocked and washed as described above.

Following formation of the antibody-analyte-antibody sandwich, HRP reporter was bound to label HRP. Streptavidin-HRP (Amersham) bound to the biotinylated secondary antibodies on the chip as recommended by the manufacturer. As above, detection was by microwave PS-3 chemiluminescence.

Figure 8:
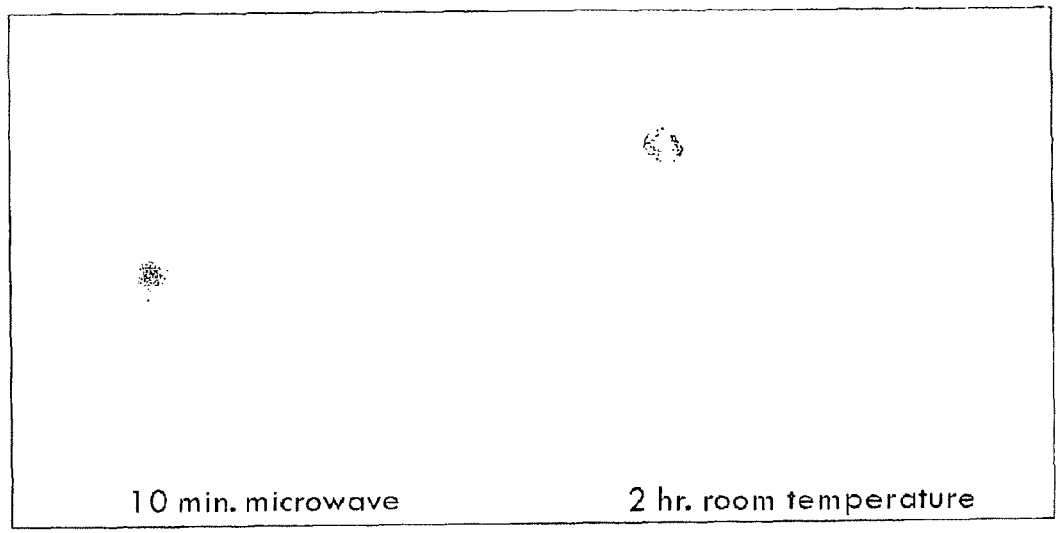
FIG. 8: Microwave-accelerated specific antibody-antigen binding (microwave-induced chemiluminescence detection).

Detection on X-ray film (Hyperfilm ECL) showed that, consistent with the results above, microwave incubation dramatically accelerated binding rates. One could easily detect both cytokines with microwave incubations and standard room temperature incubations, but could barely see the analytes with short room temperature incubations (FIG. 8).

Example 9

Microwave Chemiluminescence Detection of DNA

Experiments were performed an experiment to see if one could use microwave chemiluminescence to detect nucleic acids, such as DNA. The goal of the experiment was to detect a linear 4 kb plasmid containing a 1 kb insert of the mouse glyceraldehydes 3-phosphate dehydrogenase (GAPDH) gene. A modification of the method described in Stillman & Tonkinson (2000) was employed.

In an Eppendorf tube, DNA was reacted with psoralen-biotin (BrightStar, Ambion, Inc., Austin, Tex.) according to manufacturer's directions. The labeled DNA (1 ng/mL) was then spotted on S&S FAST Slides at volumes ranging from 0.1-1.0 µL. After drying (about 1 hour), the chips were covered with hybridization chambers (S&S) and were blocked with S&S Wash/Block Buffer for 2 hours on an orbital rocker. The chips were then washed three times in PBS/0.1% Tween buffer (10 min/wash) and two times in PBS buffer (10 min/wash). After washing, streptavidin-HRP (Amersham) was added at dilutions varying from 5000:1 to 35,000:1 and rocked for 1 hour. The chips were then washed as above, but also with two quick (1 min) washes in 83 mM PIPES buffer, pH 7.0. HRP-labeled DNA was detected using PS-3 chemiluminescent substrate (Lumigen) modified for microwave chemiluminescence. An equal volume of substrate (PS-3) was mixed with either pH 5.0 citrate/phosphate/perborate (as in Example 8) or pH 7.0 PIPES/perborate. Slide-sized nitrocellulose membranes (AE100, S&S) were then wetted with substrate-containing buffer and overlaid the DNA chips with the wet, transparent membranes. After 2-3 minute incubations to allow for enzyme catalysis, the membrane-covered chips were microwaved and light emission (through the overlaid AE100 membrane) on X-ray film was detected.

Light emission was observed upon microwave irradiation (30 sec detection) but not in similar room temperature detection. This demonstrates that microwave chemiluminescence can be used to detect DNA on chips. It is estimated that 379 attomoles of DNA was detected using microwave chemiluminescence.

Example 10

Microwave-Accelerated Nucleic Acid Hybridization

Experiments were performed to test whether mild microwave irradiation can accelerate nucleic acid-nucleic acid hybridization. Nucleic acid hybridization is an important step in DNA and RNA testing in plates and microarray chips.

A plate-based mRNA quantitation kit from R&D Systems (Quantikine mRNA, Cat. RN000, Minneapolis, Minn.) was used. The assay kit includes all reagents except for specific detection probes and analytes ("targets"). Probes and calibrator for human β-actin (Genbank Accession 3NM001101.2, cDNA=866 bp, Cat# RN188)) and human COX-2 (Genbank Accession NM_000963, cDNA=4465 bp, Cat# RN171-036) were purchased from R&D Systems. In the experiments, β-actin mRNA was used as the analyte (target) and COX-2 mRNA as the control.

The assay format involved a "sandwich" type hybridization where the target mRNA was hybridized at both ends to gene-specific probes. One probe is biotinylated to allow capture on a solid phase streptavidin-coated 96-well plate. The other probe is labeled with digoxigenin to allow binding of the reporter-generating molecule. The reporter-generating molecule is a conjugate of an anti-digoxigenin antibody and alkaline phosphatase (AP). The kit is sold for colorimetric detection, but hybridized mRNA was detected using a luminescent AP substrate (CDP-Star with Nitroblock II, Applied Biosystems, Bedford, Mass.).

Hybridization was performed in four plates ( )—two plates were incubated in a 65° C. water bath and two plates were undercoated with Emerson & Cuming BSR-1 dielectric and mildly microwaved. The specific procedure was as follows.

First, β-actin probes were mixed with a range of calibrators (0-400 amol/mL COX-2 and 0-150 amol/mL β-actin) in four 96-well plates (Costar 3590) using kit buffers according to manufacturer instructions. Two of the plates (for microwaving) were undercoated with Emerson & Cuming BSR-1 dielectric (0.01" thick). Each plate was incubated separately; (1) in a 65° C. water bath for 60 minutes, (2) in a 65° C. water bath for 10 minutes, (3) 10 minute microwave (600 W intermittent), and (4) 5 minute microwave (600 W intermittent). For microwave incubations, the plate temperature held at approximately 55° C. Following incubations solution was transferred to wells of a streptavidin-coated plate (part of kit) and allowed binding of biotinylated nucleic acid. Following binding, anti-digoxigenin-AP conjugate was washed and added, and allowed to bind. After additional washes, CDP-Star substrate was added to the wells. After a suitable 5 minute incubation, the chemiluminescence was read in a standard luminometer (Luminoskan Ascent, Thermo LabSystems).

Figure 11:
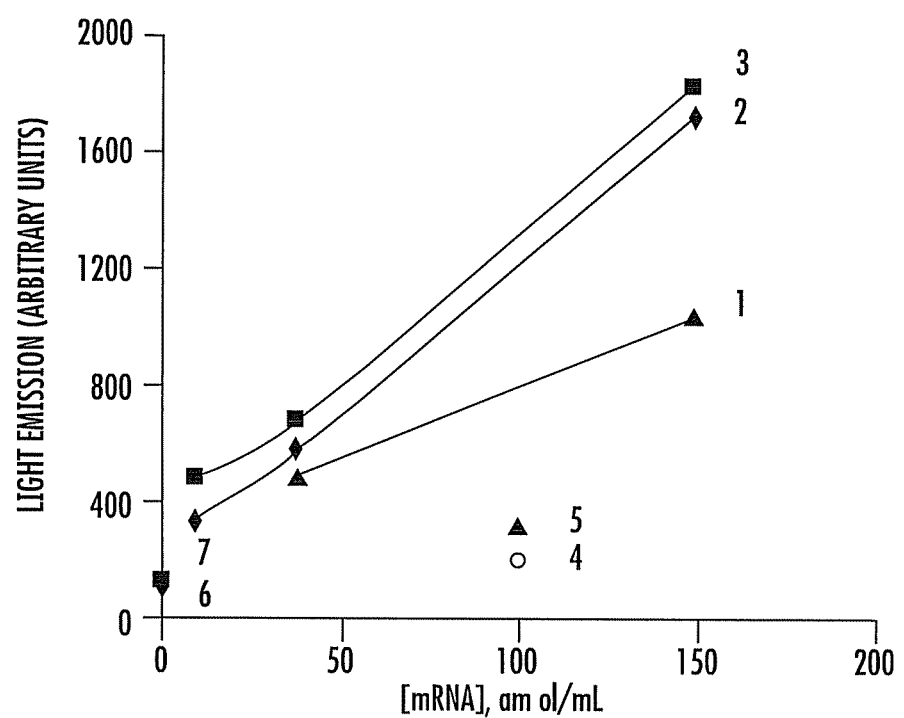
FIG. 11: Microwave-accelerated specific nucleic acid hybridization used in an assay for Human Actin mRNA: 1. Actin mRNA, 10 min, 65° C. water bath; 2. Actin mRNA, 60 min, 65° C. water bath; 3. Actin mRNA, 10 min, microwave; 4. Control Cox-2 mRNA, 60 min, 65° C. water bath; 5. Control Cox-2 mRNA, 10 min, microwave; 6. Control no mRNA, 60 min, 65° C. water bath; 7. Control no mRNA, 10 min, microwave.

Results showed that microwave incubation (55° C.) is quicker than water bath incubation (65° C.)(FIG. 11). Controls (COX-2 or no mRNA) gave little or no signal, but β-actin mRNA gave strong signals. Signals were not seen with 5-minute microwave incubation, but this was believed to be an artifact. These results indicate that mild microwaving provides at least six-fold faster hybridization of nucleic acids than waterbath incubation.

This experiment was repeated (10 minute microwave and 60 minute waterbath) with essentially the same result.

Example 11

Microwave-Accelerated PCR

Directed microwave heating can be used to accelerate DNA amplification by PCR (Newton & Graham, 1997; McPherson & Moller, 2000). The sample of DNA to be amplified and PCR reagents are placed in a dielectric-coated vessel (such as a PCR tube) or on a dielectric-coated chip (such as described in Giordano et al., 2001). Other formats are possible as long as they have a reaction surface that is in thermal contact with a microwave-targeted dielectric. DNA can be immobilized on a surface solid phase or in solution proximal to the dielectric. Results described in Example 10 demonstrated that nucleic acid hybridization occurs faster in a dielectric-coated vessel than in a vessel at the same (or higher) temperatures. Thus, the dielectric coating is essential for the invention.

DNA can be amplified in a SiC dielectric-coated PCR tube. The tube is prepared by mixing SiC powder (400 grit) with Elmer's Glue-All (aqueous-based PVAc). The mixture is painted on the surface of the tube and allowed to dry.

The DNA to be amplified can be a sequence of choice but for example can be a 500-base-pair-fragment of DNA from λ phage (Giordano et al., 2001). Appropriate oligos are prepared.

The procedure that is followed is similar to that described as Protocol 2.1 in McPherson & Moller (2000) except that a microwave oven (600 W, 2450 MHz) is used instead of a thermocycler to vary the temperature and the cycle times are different. All reagents and other equipment are as described. Below is shown the recommended thermocycler temperatures and time regime for a cycle of amplification:

(a) 94° for 5 min (to denature the template);
(b) 94° for 1 min;
(c) 55° for 1 min;
(d) 72° for 1 min; (repeat (b)-(d) 25-40 times;
(e) 72° for 2 min (to ensure all molecules are completely synthesized).

Reagent temperatures under microwave conditions are held essentially the same. Temperatures can be monitored using an IR optical pyrometer. Microwave incubation times are 10-fold shorter. Minor optimization of the microwave protocol may be required which will involve shortening incubation times 10-fold at each individual temperature, while holding the other incubation times for the other temperatures as listed above. For example, steps (a)-(b) (at 94°) are shortened from 360 seconds to 36 seconds while the other steps are held as shown above. DNA yields are measured by conventional means. Steps that that can be shortened without substantially impairing the final yield of amplified DNA are shortened in the final optimized microwave protocol.

Example 12

Microwave-Accelerated Tissue Microarray Analysis

Tissue microarrays are thin sections of normal or diseased human, animal, or plant issue generally placed on microscope slides or cards (Simon et al., 2004; Dutton 2003). The presence and distribution of molecular species on the arrays can be probed with specific antibodies or single stranded nucleic acids. Biospecific binding of a probe to a tissue microarray obeys the same physicochemical principles as binding to a molecular microarray chip. Mild microwave irradiation can accelerate biospecific molecular binding to a tissue array. In addition, detection can be carried out using microwave chemiluminescence.

Tissue microarrays can be made by the user or purchased from a vendor. IMGENEX Corp. (San Diego, Calif.) is a major vendor of ready-made tissue array slides, brand named Histo™-Array Slides. Microwave incubation and detection of human TNFα can be performed on Histo™-Array Slides;

such as formalin-fixed human tumor tissue slides (e.g., Cat. #'s IMH-301, IMH-304, IMH-306).

The manufacturer's (IMGENEX) instructions are followed except where for directed microwave incubation and detection steps. Prior to being used in directed microwave incubation/detection, the slides are undercoated with BSR-1 dielectric. Binding of the primary antibody (1 µg/mL biotinylated mouse anti-human TNFα monoclonal antibody, BD Pharmingen, Cat#554551) is accelerated by intermittent microwaving (600 W, 2450 MHz) for 10 minutes at 35-45° C. This is 12-fold shorter time than the manufacturer (IMGENEX) recommended binding time of 120 minutes at room temperature. Following binding, the slides are washed and incubated with streptavidin-HRP (500:1 dilution, Amersham). Detection of the enzyme HRP (and hence TNFα) is carried out by microwave chemiluminescence using the formula (Lumigen PS-3) and method described above.

Similarly, in situ hybridization (detection of specific RNA) can be carried out on tissue microarrays. Again, the IMGENEX protocol is followed except for rapid microwave-accelerated hybridization and microwave chemiluminescence. The probe hybridization step is carried out on a dielectric (BSR-1)-undercoated slide for 60 minutes in a microwave oven (600 W, 2450 MHz, slide maintained at 45-55° C.). This is 16-fold shorter than the vendor recommended time of 16 hours in a 50° C. incubator.

Example 13

Microwave-Accelerated Cytokine Analysis Using Fluorescence Detection

Microwave-accelerated binding was compared to room temperature binding of nine cytokines to capture antibodies on nitrocellulose chips. This experiment was carried out using a Schleicher & Schuell FASTQuant kit, which can be used to analyze the presence and concentrations of human IL-10, IL-13, IFNγ, IL-1β, IL-2, IL-4, IL-5, IL-6, and TNFα. The chips are sold with pre-printed specific capture antibodies for these cytokines printed on each slide.

Each chip has 16 assay pads, each consisting of a 6×6 antibody array. The arrangement of capture antibodies within each assay pad is shown below:

|   | 1 | 2 | 3 | 4 | 5 | 6 |
|---|---|---|---|---|---|---|
| 1 | positive control | positive control | positive control | IL-6 | IL-6 | IL-6 |
| 2 | IL-1β | IL-1β | IL-1β | IL-10 | IL-10 | IL-10 |
| 3 | IL-2 | IL-2 | IL-2 | IL-13 | IL-13 | IL-13 |
| 4 | IL-4 | IL-4 | IL-4 | IFNγ | IFNγ | IFNγ |
| 5 | IL-5 | IL-5 | IL-5 | TNFα | TNFα | TNFα |
| 6 | positive control | positive control | positive control | positive control | positive control | positive control |

The reaction pads on a chip can be spatially partitioned S&S 16-well chambers, thus allowing each 6×6 array to be individually assayed. Four chips were assayed, each with eight assay zones used. One each chip standard curves consisting of eight cytokine concentrations were tested. The eight zones had the following cytokine cocktails:

| Reaction Zone | IL-10, IL-13, IFNγ (pg/mL) | IL-1β, IL-2, IL-4, IL-5, IL-6, TFNα (pg/mL) |
|---|---|---|
| 1 | 50,000 | 10,000 |
| 2 | 12,500 | 2,500 |
| 3 | 3,125 | 625 |
| 4 | 781.25 | 156.25 |
| 5 | 195.31 | 39 |
| 6 | 48.83 | 9.76 |
| 7 | 12.2 | 2.44 |
| 8 | 0 | 0 |

Two chips were assayed according to manufacturer's instructions (and using included kit reagents and buffers) with one exception. The other two chips were also assayed according to the same instructions, but with one exception. Instead of the recommended room temperature capture of cytokines on capture antibodies for 3 hours, chips were undercoated with Emerson & Cuming BSR-1 dielectric (0.01" thick) and intermittently microwaved for 15 minutes. Microwaving (600 W GE microwave) was monitored using an infrared thermometer and the chip temperatures were maintained between 30 and 42° C. To maintain this range, microwaves were pulsed with a sequence of roughly approximated 3 seconds on and 90 seconds off.

All secondary antibodies (included in kit) were labeled with streptavidin-$Cy^5$ (Amersham Biosciences) as recommended by S&S and chips were scanned with a GenePix fluorescence microarray scanner (Axon Instruments, Inc., Union City Calif.).

Figure 9:
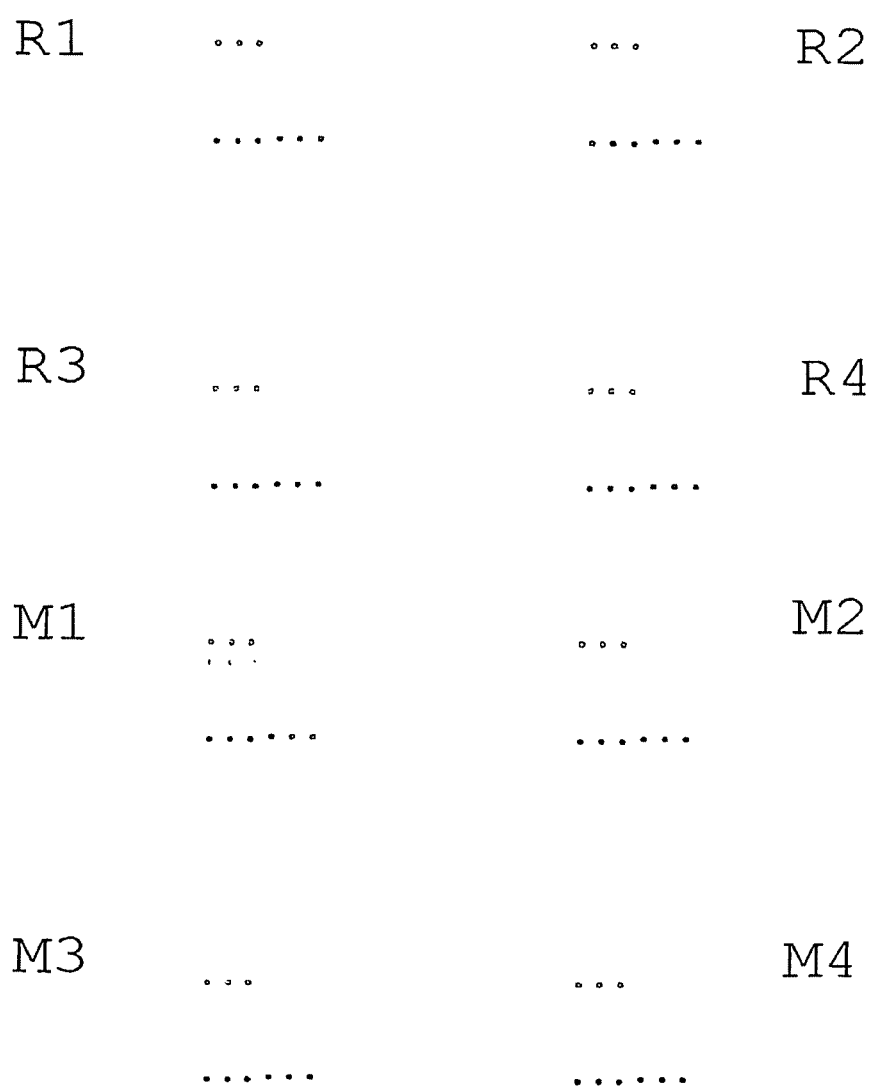
FIG. 9: Microwave-accelerated specific antibody-antigen binding (fluorescence detection).
Figure 10:
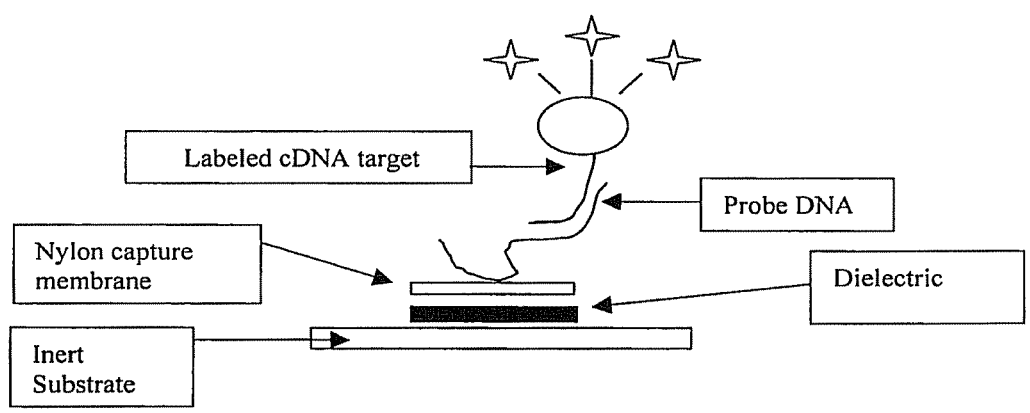
FIG. 10: A typical nucleic acid assay.

Results showed that a 15-minute microwave incubation gave brighter spots (with minimal background) than a 3 hour incubation at room temperature. FIG. 9 shows digitized scans from a room temperature chip (R1-R4) and a microwave chip (M1-M4). The numbers 1-4 refer to the reaction zones (see above).

These results are important in that they show the universality of accelerated microwave binding—all nine cytokines bound better under directed microwave binding than at room temperature. All of the analytes have different molecular structures and unique binding specificities. The results also show that fluorescence monitoring can be used.

References

Below is a list of publications cited herein:
ASTM Committee E20 on Temperature Measurement (1993) ASTM, Philadelphia.
Blackwell, H. E. (2003) Org. Biomol. Chem. 1, 1251-1255.
Boon, M. E. & Kok, L. P. (1989) in Microwave Cookbook of Pathology, Coulomb Press, Leiden.
Borman, S. (2001) Chem. Engin. News 79 (35) 49-58.
Bose, A. K. et al. (1997) CHEMTECH 27(9), 18-25.
Bradley, D. (2001) Modern Drug Discovery 4(8), 32-36.
Bram, G., Loupy, A., Majdoub, M., Gutierrez, E., & Ruizitky, E. (1990) Tetrahedron 46, 5167.
Bram, G., Loupy, A., Majdoub, M., and Petit, A. (1991) Chem. Ind. 396.
Chen, S.-H. (2003) PharmaGenomics 3 (8) 56-63.
Constans, A. (2003) The Scientist. November, pp. 43-45.
Cooper, C. S. (2001) Breast Cancer Res. 3, 158-175.
Dolle, R. E. (2000) J. Comb. Chem. 2, 383-433.
Draghici, S. et al. (2001) Curr. Opin. Drug Discov. Dev. (2001) 4, 332-337.
Ewart, T. G. & Gavin, G. T. (1999) Nanoparticles Biosensor, U.S. Pat. No. 5,922,537.
Fermer, C., Nilsson, P., & Larhead, M. (2003) Eur. J. Pharm. Sci. 18, 129-132.

Fodor, S. P. A., Rava, R. P., Huang, X. C., Pease, A. C., Holmes, C. P., & Adams, C. L. (1993) Nature 364(6437), 555-556.
Freeman, W. M., Walker, S. J., & Vrana, K. E. (1999) BioTechniques 26, 112-125.
Gabriel, C., Gabriel, S., Grant, E. H., Halstead, B. S. J., Mingos, D. M. P. (1998) Chem. Soc. Rev. 27, 213-224.
Giordano, B. C., Ferrance, J., Swedberg, S., Huhmer, A. F. R., & Landers, J. P. (2001) Anal. Biochem. 291, 124-132.
Gloffke, W. (2003) The Scientist 17 (8) 41-43.
Hjerpe, A., Boon, M. E., & Kok, L. P. (1988) 20, 388-396.
Holworth, A. et al. Ind. Eng. Chem. Res. (1998) 37, 2701.
Huhmer, A. F. R. and Landers, J. P (2000) Anal. Chem. 72, 5507-5512.
Jain, S., Sharma, S., & Gupta, M. N. (2002) Anal. Biochem. 311, 84-86.
Jin, Q. et al. (1999) Trends Anal. Chem. 18, 479-484.
Johnson, B. (1999) The Scientist 13, 16.
Kappe, C. O. (2001) American Laboratory 23, 13-19.
Kappe, C. O. (2002) Curr. Opin. Chem. Biol. 6, 314-320.
Kidwai, M., Kohli, S., Saxena, R. K., Gupta, R., and Bardoo, S. (1998) Ind. J. Chem. 37B, 963.
Kok, L. P. & Boon, M. E. (1990) Histochem. J. 22, 381-388,
Kramer, A. & Schneider-Mergener (1998) Methods Mol. Biol. 87, 25-39.
Kreider, K. G. (1989) Thin Film Thermocouples For High Temperature Measurement. NIST, Springfield, Va.
Kricka, L. J. (1999) Clin. Chem. 45, 453-8.
Kubrakova, I. V. (2000) J. Anal. Chem. 55, 1113-1122.
Laslo, T. S. (1980) The Physics Teacher, November, 570-579.
Latchman, D. S. (1995) PCR Applications in Pathology. Principles and Practice. New York, Oxford Univ. Press.
Lennon, G. G. (2000) Drug Discov. Today 5, 59-66.
Leong, A. S.-Y. & Milios, J. (1986) J. Pathol. 148, 183-187.
Lew, A., Krutzik, P. O., Hart, M. E., & Chamberlain, A. R. (2002) J. Comb. Chem. 4, 95-105.
Lidstrom, P., Tierney, P., Walthey, B., & Westman, J. (2001) Tetrahedron 57, 9225-9283.
MacBeath, G., Koehler, A. N., & Schreiber, S. L. (1999) J. Am. Chem. Soc. 121, 7967-7968.
McPherson, M. J. & Moller, S. G. (2000) PCR. Bios Scientific Publishers, Oxford, UK.
Maugard, T., Gaunt, D., Legoy, M. D. & Besson, T. (2003) Biotechnol. Lett. 25, 623-629.
Mingos, D M P & Baghurst, D R (1991) Chem. Soc. Rev. 20, 1-47.
Nataranjan, M., Vijayalaxmi, Szilagyi, M., Roldan, F. N., & Meltz, M. L. (2002) Bioelectromagnetics 23, 271-277.
Nesatyy, V. J., Dacanay, A., Kelly, J. F., & Ross, N. W. (2002) Rapid Commun. Mass Spectrom. 16, 272-280.
Newton, C. R. & Graham, A. (1994) PCR. Springer-Verlag, New York,
Pasinetti, G. M. (2001) J. Neurosci. Res. 65, 471-476.
Price, C. P. & Newman, D. J. (1997) Principles and Practice of Immunoassay 2nd Ed. Macmillan, London,
Schena, M., Shalon, D., Davis, R. W., & Brown, P. O. (1995) Science 270, 467-470.
Schmalzing, D. et al. (2000) Electrophoresis 21, 3919-3930.
Seiden, M. L. & Sklar, J. L. (1996) in Important Advances In Oncology, D. T. DeVita, ed., Philadelphia, Lippincott-Raven.
Slap, S. E. (2003) Am. Biotechnol. Laboratory, November, 40.
Slyanev, M. N. (2001) Anal. Chem. 73, 4037-4044.
Stillman, B. A. & Tonkinson, J. L. (2000) BioTechniues 29, 630.
Surrmeijer, A. J. H., Boon, M. E., & Kok, L. P. (1990) Histochem. J. 22, 341-346.
Van den Brink, W. J., Zijlmans, H. J. M. A. A., Kok, L. P., Bolhuis, P., Volers, H. H., Boon, M. E., & Houthoff, H. J. (1990) Histochem. J. 22, 327-334.
Van de Kant, H. I. J., Boon, M. E., & de Rooij, D. G. (1988) Histochem. J. 20, 3350340.
Varma, R. (2001) AMPERE Newsletter, Issue 29, ISSN 1361-8598.
Wathey, B., Tierney, J., Lidstrom, P., & Westman, J. (2002) Drug Discovery Today 7, 373-380,
Wild, D. (2000) Immunoassay Handbook $2^{nd}$ Ed. Macmillan, London.
Yang, P. et al. (1998) Science 282, 2244.
Zlotorzynski, A. Crit. Rev. Anal. Chem. (1995) 25, 43.
Zubritsky, E. (2001) Modern Drug Discov., May issue, 59-71.

All publications and patents mentioned in this specification are herein incorporated by reference to the same extent as if each individual publication or patent application was specifically and individually indicated to be incorporated by reference in the entirety.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for accelerating a biospecific binding reaction involving one or more reactant(s) and a carrier fluid, wherein the one or more reactant(s) comprises one or more nucleic acid(s), said method comprising:
    (a) contacting a composite material with said reactant(s) and carrier fluid, said composite material comprising a solid material susceptible to microwave heating and capture molecules, wherein the capture molecules comprise one or more nucleic acid(s), said contacting being under conditions sufficient to allow said reactant(s) to bind to said capture molecule(s) of said composite via a biospecific interaction;
    (b) applying an electromagnetic field to said composite material, wherein the wavelength of the electromagnetic field is between 1 cm and 100 m and is sufficient to result in microwave heating of said solid material; and
    (c) allowing said composite material to transfer heat to said reactant(s);
    (d) whereby a product is formed from said reactant(s) and said capture molecule(s) at a greater rate than without heating from the heated composite material, thereby accelerating said biospecific binding reaction.

2. The method of claim 1, wherein said biospecific binding reaction comprises hybridization of two nucleic acid molecules to one another.

3. The method of claim 1, wherein said biospecific binding reaction comprises a nucleic acid amplification reaction.

4. The method of claim 3, wherein the amplification reaction is a polymerase chain reaction.

5. The method of claim 1, further comprising the step of measuring the extent or rate of said biospecific binding reaction.

6. The method of claim 5, wherein the measuring is by absorbance, chemiluminescence, or fluorescence detection.

7. The method of claim 1, wherein the solid material is incorporated into a device selected from a group consisting of a microarray chip/slide, microtiter plate, Petri dish, centrifuge tube, and test tube.

8. The method of claim 1, wherein the biospecific binding reaction occurs on a surface of a particle, bead, or spot.

9. The method of claim 1, further comprising the steps of:
(e) contacting said composite with one or more additional reactant(s) capable of participating in a biospecific interaction with (i) said reactant(s) from step (a) or (ii) said product produced as a consequence of said biospecific binding reaction involving said reactant(s) from step (a);
(f) allowing said additional reactant(s) to react in said biospecific interaction; and
(g) measuring the extent or rate of said biospecific interaction.

10. The method of claim 9, wherein said one or more additional biospecific binding reaction(s) comprises hybridization of two nucleic acid molecules.

11. The method of claim 9, wherein the measuring is by absorbance, chemiluminescence, or fluorescence detection.

12. The method of claim 9, wherein the solid material is incorporated into a device selected from a group consisting of a microarray chip/slide, microtiter plate, Petri dish, centrifuge tube, and test tube.

13. The method of claim 9, wherein the biospecific binding reaction occurs on a surface of a particle, bead, or spot.

14. The method of claim 1, further comprising the acceleration of one or more additional biospecific binding reactions involving one or more reactant(s), said method comprising the additional steps of:
(e) contacting said composite with one or more additional reactant(s), wherein said additional reactant(s) are capable of participating in said one or more additional biospecific binding reactions involving (i) said reactant(s) from step (a) or (ii) said product produced as a consequence of said biospecific binding reaction involving said reactant(s) from step (a);
(f) applying an electromagnetic field wherein the wavelength of the applied field is between 1 cm and 100 m to said composite, said electromagnetic field being sufficient to result in microwave heating of said solid material, said additional reactant(s) being heated by heat transfer from said heated solid material; and
(g) allowing said heated additional reactant(s) to react with either (i) said reactant(s) from step(a) or (ii) said product produced as a consequence of said biospecific binding reaction involving said reactant(s) from step(a), whereby an additional product is formed from (iii) said additional reactant(s) and said reactant(s) from step (a) or (iv) said product produced as a consequence of said biospecific binding reaction involving said reactant(s) from step (a) at a greater rate than without heating from the heated composite material, thereby accelerating said biospecific binding reaction.

15. The method of claim 14, wherein said one or more additional biospecific binding reaction(s) comprises hybridization of two nucleic acid molecules.

16. The method of claim 14, wherein said one or more additional reaction(s) comprises a nucleic acid amplification reaction.

17. The method of claim 16, wherein said amplification reaction is a polymerase chain reaction.

18. The method of claim 14, further comprising the step of measuring the extent or rate of said biospecific binding reaction.

19. The method of claim 18, wherein the measuring is by absorbance, chemiluminescence, or fluorescence detection.

20. The method of claim 14, wherein the solid material is incorporated into a device selected from a group consisting of a microarray chip/slide, microliter plate, Petri dish, centrifuge tube, and test tube.

* * * * *